(12) United States Patent
Parikh et al.

(10) Patent No.: US 9,393,243 B1
(45) Date of Patent: Jul. 19, 2016

(54) TOPICAL CIPROFLOXACIN COMPOSITIONS

(71) Applicants: Nilesh Parikh, Irvine, CA (US); William Crawford Hite, Winchester, CA (US)

(72) Inventors: Nilesh Parikh, Irvine, CA (US); William Crawford Hite, Winchester, CA (US)

(*) Notice: Subject to any disclaimer, the term of this patent is extended or adjusted under 35 U.S.C. 154(b) by 0 days.

(21) Appl. No.: 14/799,270

(22) Filed: Jul. 14, 2015

(51) Int. Cl.
| | |
|---|---|
| *A61K 9/00* | (2006.01) |
| *A61K 31/496* | (2006.01) |
| *A61K 47/02* | (2006.01) |
| *A61K 47/18* | (2006.01) |
| *A61K 47/12* | (2006.01) |
| *A61K 47/38* | (2006.01) |
| *A61K 47/32* | (2006.01) |
| *A61K 45/06* | (2006.01) |
| *A61K 31/573* | (2006.01) |

(52) U.S. Cl.
CPC .............. *A61K 31/496* (2013.01); *A61K 9/0014* (2013.01); *A61K 31/573* (2013.01); *A61K 45/06* (2013.01); *A61K 47/02* (2013.01); *A61K 47/12* (2013.01); *A61K 47/183* (2013.01); *A61K 47/186* (2013.01); *A61K 47/32* (2013.01); *A61K 47/38* (2013.01)

(58) Field of Classification Search
CPC .... A61K 9/0014; A61K 31/164; A61K 38/17
USPC ........................................................ 424/400
See application file for complete search history.

(56) References Cited

U.S. PATENT DOCUMENTS

| | | | |
|---|---|---|---|
| 5,023,257 A | 6/1991 | Pollinger et al. | |
| 5,965,549 A | 10/1999 | Purwar et al. | |
| 6,284,804 B1* | 9/2001 | Singh .................. | A61K 9/0043 424/78.04 |
| 8,034,817 B2 | 10/2011 | Endermann et al. | |
| 2007/0049552 A1* | 3/2007 | Babu ..................... | A61K 9/0014 514/58 |
| 2009/0082337 A1 | 3/2009 | Venkatesh | |

FOREIGN PATENT DOCUMENTS

WO      WO9001933      3/1990

OTHER PUBLICATIONS

Axel Dalhoff, Will Stubbings, and Sabine Schubert. Comparative in Vitro Activities of the Novel Antibacterial Finafloxacin against Selected Gram-Positive and Gram-Negative Bacteria Tested in Mueller-Hinton Broth and Synthetic Urine. Antimicrobial Agents and Chemotherapy. (2011) 55(4):1814-1818.
NJ Irwin, CP McCoy, and L Carson. Effect of pH on the in vitro susceptibility of planktonic and biofilm-grown Proteus mirabilis to the quinolone antimicrobials. Journal of Applied Microbiology. (2013) 115:382-389.
Maxwell, A. The molecular basis of quinolone action. Journal of Antimicrobial Chemotherapy. (1992) 30, 409-416.
Heddle, J and Maxwell A. Quinolone-Binding Pocket of DNA Gyrase: Role of GyrB Antimicrobial Agents and Chemotherapy. (2002) 46:6, 1805-1815.
Barnard, F. and Maxwell, A. Interaction between DNA Gyrase and Quinolones: Effects of Alanine Mutations at GyrA Subunit Residues Ser and Asp87. Antimicrobial Agents and Chemotherapy. (2002) 45:7, 1994-2000.
Bedard and Bryan. Interaction of the Fluoroquinolone Antimicrobial Agents Ciprofloxacin and Enoxacin with Liposomes. Antimicrobial Agents and Chemotherapy. (1989) 33:8, 1349-1382.

\* cited by examiner

*Primary Examiner* — Johann R Richter
*Assistant Examiner* — Yanzhi Zhang

(57) ABSTRACT

Embodiments of the invention provide pharmaceutical compositions of ciprofloxacin formulated for topical application to a body surface and for having at least localized antibacterial activity. In some embodiments, the compositions are further formulated for localized anti-inflammatory activity, anti-fungal activity, anti-viral activity, or combinations thereof. Such compositions possess a therapeutically effective amount of a non-betaine form ciprofloxacin (e.g., ciprofloxacin hydrochloride monohydrate); one of a pH adjusting agent and a preservative; water; and a pH from about 5.5 to about 10. In some embodiments, such compositions may be free or free of added skin permeation enhancer and/or contain a betaine form ciprofloxacin.

16 Claims, 14 Drawing Sheets

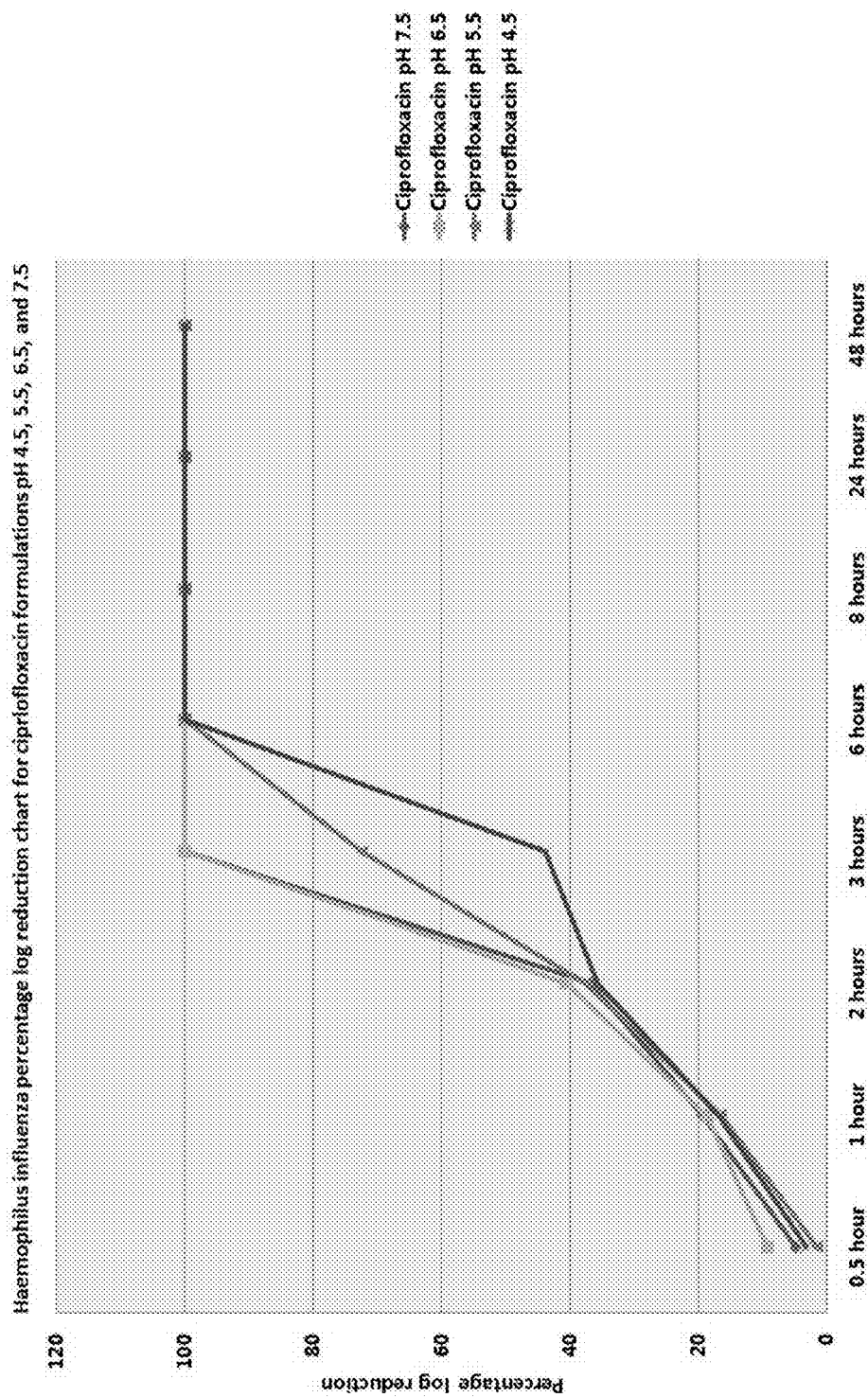

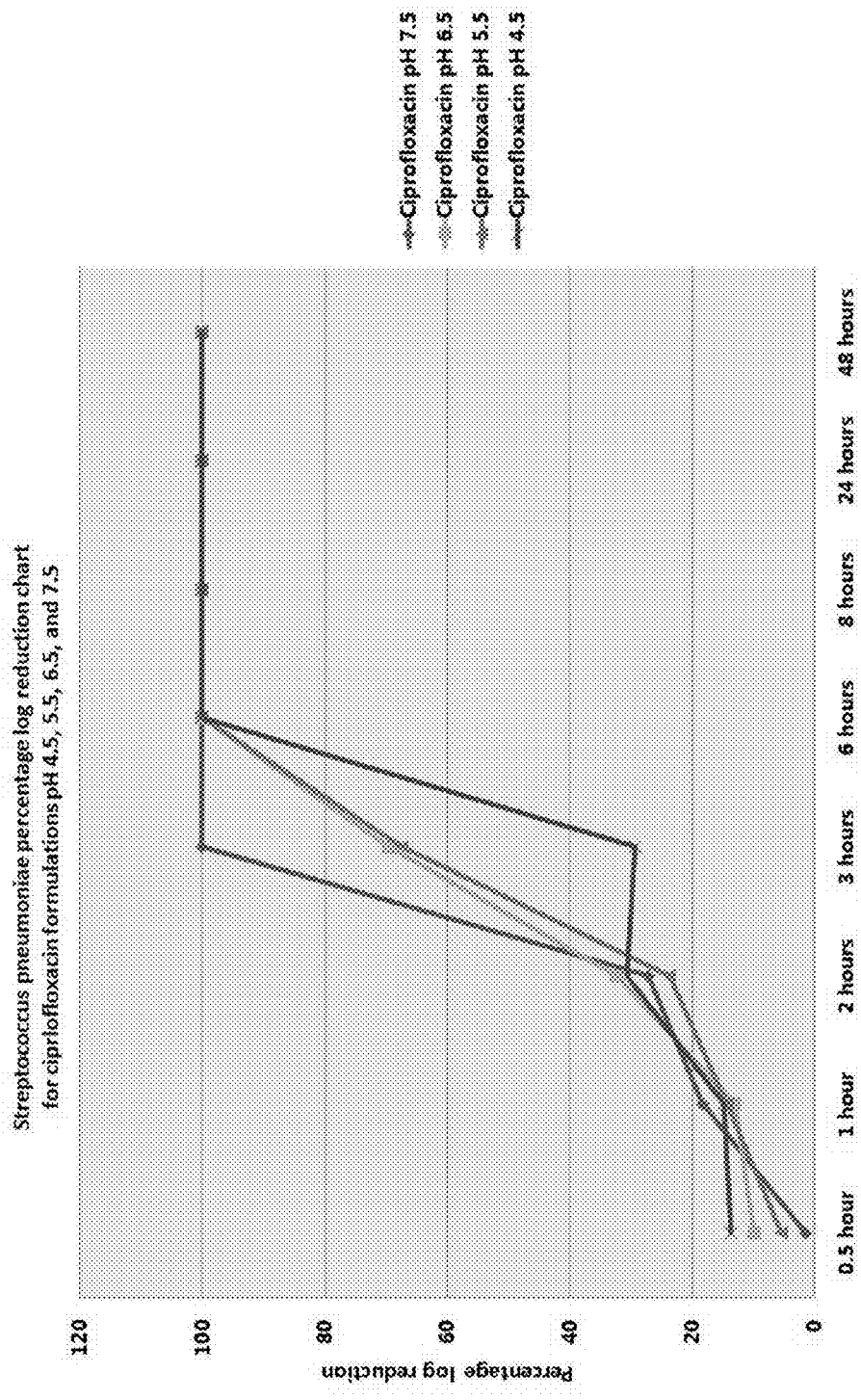

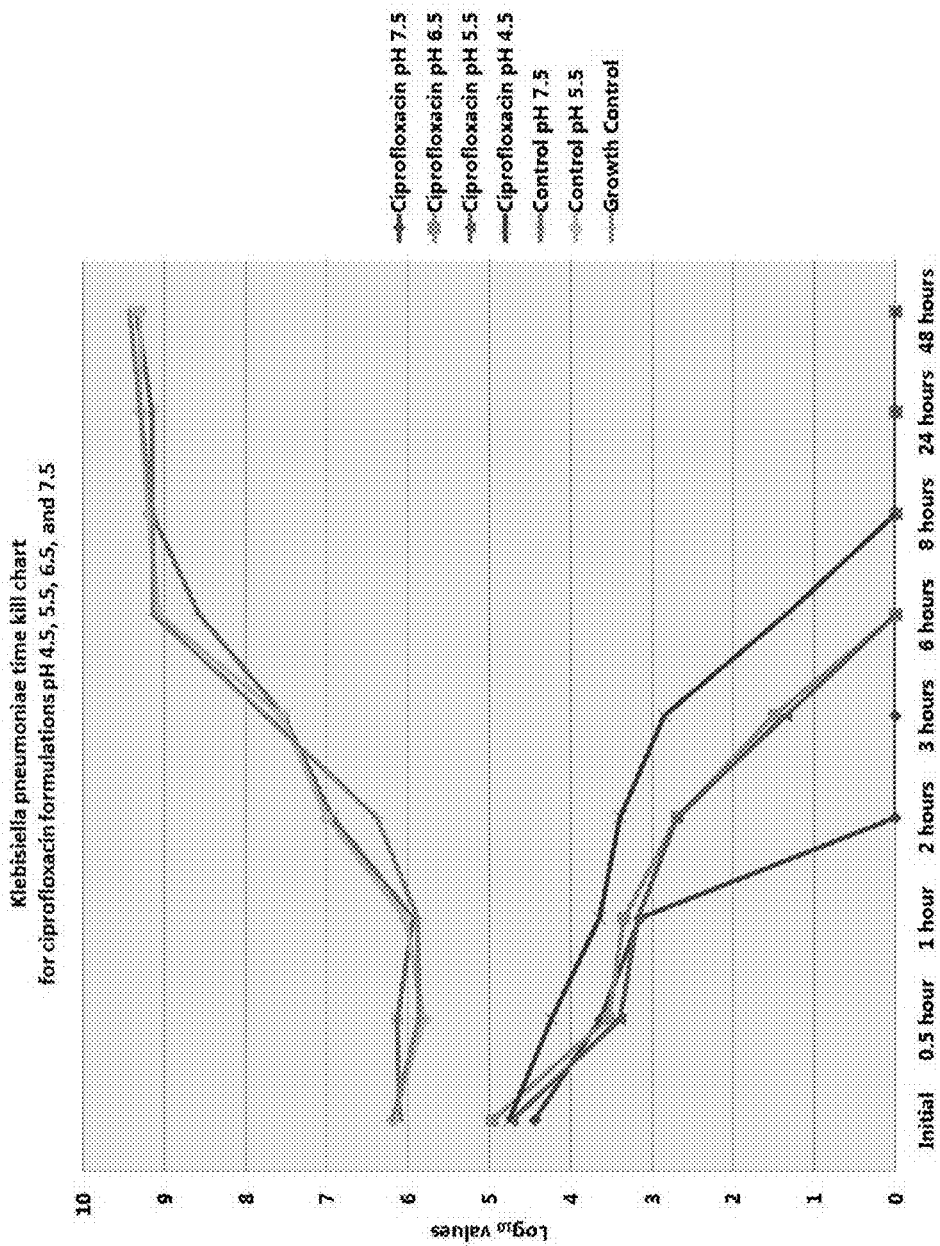

TOPICAL CIPROFLOXACIN COMPOSITIONS

FIELD OF THE INVENTION

The present invention relates to pharmaceutical ciprofloxacin compositions for topical application and localized antibacterial activity at body sites that comprise, e.g., an ear canal, an oral cavity, a pharyngeal cavity, a nasal cavity, a pulmonary cavity, a vaginal cavity, a rectal cavity, a mucosal surface, a dermal surface, an ophthalmic surface, and a fingernail surface.

BACKGROUND OF THE INVENTION

Ciprofloxacin belongs to the fluoroquinolone group of antibiotics, and is chemically known as 1-cyclopropyl-6-fluoro-1,4-dihydro-4-oxo-7-(1-piperazinyl)-3-quinolinecarboxylic acid. It possesses the chemical structure depicted in Formula 1.

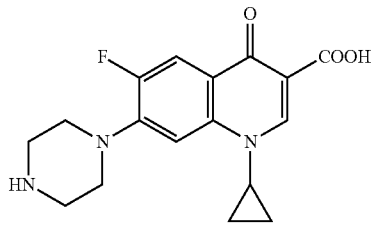

Formula I

Fluoroquinolone antibiotics such as ciprofloxacin provide advantages over other classes of antibiotics, such as possessing comparatively lower minimum inhibitory concentration required to inhibit ninety percent of a variety of bacterial pathogens ($MIC_{90}$) and engendering to a lesser degree the formation of resistant bacterial strains. For instance, ciprofloxacin typically exhibits an $MIC_{90}$ around 0.5 µg/g and the aminoglycoside antibiotic, gentamycin, typically exhibits an $MIC_{90}$ around 10 µg/gm. (See, e.g., T. L. Ke et al., *Journal of Ocular Pharmacology and Therapeutics*, Vol. 17, No. 6, p 555-562, 2001.) In addition, ciprofloxacin is a broad-spectrum antibiotic that demonstrates antibacterial activity against a wide range of both gram-negative and gram-positive bacterial species. Whereas other antibiotics, such as neomycin, polymyxin B, gentamicin and tobramycin or bacitracin, gramicidin, and erythromycin, are primarily active against gram-negative or gram-positive bacteria, respectively.

Ciprofloxacin is commercially available throughout the world, in both topical and systemic pharmaceutical formulations indicated for the treatment of bacterial infections. Examples of commercially available topical ciprofloxacin products include CILOXAN (0.3% ciprofloxacin HCl ophthalmic solution), CIPRODEX (ciprofloxacin 0.3% and dexamethasone 0.1% otic suspension), and CIPRO HC OTIC (ciprofloxacin hydrochloride and hydrocortisone otic suspension).

CILOXAN is indicated for the treatment of: i. corneal ulcers caused by infections of *Pseudomonas aeruginosa, Serratia marcescens, Staphylococcus aureus, Staphylococcus epidermidis, Streptococcus pneumoniae,* and *Streptococcus* (Viridans Group), and ii. conjunctivitis caused by infections of *Haemophilus influenzae, Staphylococcus aureus, Staphylococcus epidermidis,* and *Streptococcus pneumoniae.*

CIPRODEX is indicated for the treatment of: i. acute otitis media in pediatric patients (age 6 months and older) with tympanostomy tubes due to *Staphylococcus aureus, Streptococcus pneumoniae, Haemophilus influenzae, Moraxella catarrhalis,* and *Pseudomonas aeruginosa,* and ii. acute otitis externa in pediatric (age 6 months and older), adult and elderly patients due to *Staphylococcus aureus* and *Pseudomonas aeruginosa.*

CIPRO HC OTIC is indicated for the treatment of acute otitis externa in adult and pediatric patients, one year and older, due to *Pseudomonas aeruginosa, Staphylococcus aureus,* and *Proteus mirabilis.*

SUMMARY OF THE INVENTION

Certain embodiments of the present invention provide pharmaceutical compositions of ciprofloxacin formulated for topical application to a body site and for having at least localized antibacterial activity. In some embodiments, the compositions are further formulated with one or more additional drugs that provide for localized anti-inflammatory activity, anti-fungal activity, and/or anti-viral activity. Such compositions possess a therapeutically effective amount of a non-betaine form ciprofloxacin (e.g., ciprofloxacin hydrochloride monohydrate); at least one of a pH adjusting agent and a preservative; water; and a pH of more than 5.5 to less than 10. In some embodiments, the pH is more than or about 5.5, 5.6, 5.7, 5.75, 5.8, 5.9, or 6; about 6.5, 7, 8, 8.5, or 9; less than or about 10; or a range therebetween.

In some embodiments, the topical application site may be one or more of a dermal surface, an ophthalmic surface, a mucosal surface, and a fingernail surface, an ear canal, an oral cavity, a pharyngeal cavity, a nasal cavity, a pulmonary cavity, a vaginal cavity, and a rectal cavity. In some embodiments, such compositions are free, or substantially free, of added skin permeation enhancer. In some embodiments, such compositions further possess added betaine form ciprofloxacin.

In some embodiments, the non-betaine form ciprofloxacin is present in such compositions in an amount ranging from about 0.05% w/w to about 20% w/w of the composition; the pH adjusting agent, when present in the composition, is one or more of a hydrochloric acid, a sulfuric acid, a phosphoric acid, a sodium hydroxide, a potassium hydroxide, a calcium hydroxide, a magnesium hydroxide, and an ethanolamine; and the preservative, when present in the composition, is one or more of a benzalkonium chloride, a lauralkonium chloride, a cetrimonium, a chlorobutanol, a methyl paraben, a propyl paraben, a phenylethyl alcohol, a borate, a sorbate, in an amount ranging from about 0.01% w/w to about 2.5% w/w of the composition.

In some embodiments, the compositions may further contain one or more of an osmolality adjusting agent, a viscosity building agent, a buffer, a chelating agent, and a surfactant. In such embodiments, the osmolality adjusting agent can be one or more of a glycerol, a mannitol, a xylitol, a sorbitol, a dextrose, a glucose, a maltose, a trehalose, a sucrose, a cyclodextrin, a propylene glycol a, sodium chloride, a potassium chloride, a calcium chloride, a magnesium chloride, a sodium bisulfite, a sodium sulfite, a sodium sulfate, a sodium bicarbonate, a sodium carbonate, a sodium thiosulfate, a potassium acetate, a sodium acetate, a magnesium sulfate, a disodium hydrogen phosphate, a sodium dihydrogen phosphate, and a potassium dihydrogen phosphate.

The viscosity building agent can be one or more of a polyethylene glycol, a polyvinyl alcohol, a polyvinyl pyrrolidone, a polyvinyl alcohol, a methylcellulose, a hydroxyethylcellulose, a hydroxypropylcellulose, a guar gum, a hydroxypropyl guar gum, a gum arabic, a karaya gum, a xanthan gum, an agar, an alginic acid, a dextran, a heparin, a hyaluronic acid, a chondroitin sulfate, a starch, a chitin, a carrageenan, a polyacrylate, a casein, a gelatin, a collagen, a pectin, and an elastin.

The buffer can be on or more of a phosphate buffer, a citrate buffer, an acetate buffer, a carbonate buffer, a succinate buffer, a bicine buffer, a TRIS buffer, a tricine buffer, a TAPSO buffer, a HEPES buffer, a TES buffer, a MOPS buffer, a PIPES buffer, a cacodylate buffer, and a MES buffer.

The chelating agent can be one or more of a adeferoxamine, an ethylenediaminetetraacetic acid (EDTA), an ethyleneglycoltetraacetic acid (EGTA).

And the surfactant can be one or more of a sorbitan, a polysorbate, a poloxamer, a sodium lauryl sulfate, and a tyloxapol.

In some embodiments, ciprofloxacin compositions of the invention may be used in methods of treating a bacterial infection in a subject in need thereof. Such methods involve the step of topically applying, at least once a day, at least about 10 microliters the compositions. In such methods, the application site is infected with a ciprofloxacin susceptible bacteria; and the application site is one or more of a dermal surface, an ophthalmic surface, a mucosal surface, a fingernail surface, an ear canal, an oral cavity, a pharyngeal cavity, a nasal cavity, a pulmonary cavity, a vaginal cavity, and a rectal cavity.

Certain embodiments of the invention provide a first pharmaceutical ciprofloxacin composition formulated for topical application to a body site and for having at least localized antibacterial activity. In some embodiments, the first composition is further formulated with one or more additional drugs that provide for localized anti-inflammatory activity, anti-fungal activity, and/or anti-viral activity. In such embodiments, the first composition possesses a therapeutically effective amount of a non-betaine form ciprofloxacin (e.g., ciprofloxacin hydrochloride monohydrate), more than 5% of which is in suspended form; one or more of a pH adjusting agent and a preservative; water; and a pH of more than 5.5 to less than 10. In some embodiments, the pH is more than or about 5.5, 5.6, 5.7, 5.75, 5.8, 5.9, or 6; about 6.5, 7, 8, 8.5, or 9; less than or about 10; or a range therebetween.

In such embodiments, the topical application site is at least one of a dermal surface, an ophthalmic surface, a mucosal surface, a fingernail surface, an ear canal, an oral cavity, a pharyngeal cavity, a nasal cavity, a pulmonary cavity, a vaginal cavity, and a rectal cavity. In such embodiments, the first composition can be free, or substantially free, of added skin permeation enhancer. In such embodiments, the first composition can further contain added betaine form ciprofloxacin. And in such embodiments, the first composition possesses a more rapid onset of antibacterial activity than a second pharmaceutical composition that differs from the first composition by having: a pH of about 4.5 and 5% or less of the non-betaine form ciprofloxacin in suspended form.

In such embodiments, the pH of the first composition can be more than or about 5.5, 5.6, 5.7, 5.75, 5.8, 5.9, or 6; about 6.5, 7, 8, 8.5, or 9; less than or about 10; or a range therebetween. In such embodiments, the amount of non-betaine form ciprofloxacin in suspended form can be more than 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, of the total amount of non-betaine ciprofloxacin in the composition, or a range therebetween. In certain of such embodiments, the more rapid onset of anti-bacterial activity comprises the first composition exhibiting, at a time within about 6 hours, preferably 3 hours, of starting a bacterial kill rate assay, a bacterial percentage log reduction in the kill rate assay that is at least 1.5-fold greater, 1.75-fold greater, or about 2-fold greater than the second composition.

In such embodiments, the ciprofloxacin can be present in the first compositions in an amount ranging from about 0.05% w/w to about 20% w/w of the composition; the pH adjusting agent can be one or more of a hydrochloric acid, a sulfuric acid, a phosphoric acid, a sodium hydroxide, a potassium hydroxide, a calcium hydroxide, a magnesium hydroxide, and an ethanolamine; and the preservative can be one or more of a benzalkonium chloride, a lauralkonium chloride, a cetrimonium, a chlorobutanol, a methyl paraben, a propyl paraben, a phenylethyl alcohol, a borate, and a sorbate.

In certain of such embodiments, the first composition may further contain an osmolality adjusting agent, a viscosity building agent, a buffer, a chelating agent, a surfactant, or a combination thereof. In such embodiments, the osmolality adjusting agent can be one or more of a glycerol, a mannitol, a xylitol, a sorbitol, a dextrose, a glucose, a maltose, a trehalose, a sucrose, a cyclodextrin, a propylene glycol a, sodium chloride, a potassium chloride, a calcium chloride, a magnesium chloride, a sodium bisulfite, a sodium sulfite, a sodium sulfate, a sodium bicarbonate, a sodium carbonate, a sodium thiosulfate, a potassium acetate, a sodium acetate, a magnesium sulfate, a disodium hydrogen phosphate, a sodium dihydrogen phosphate, and a potassium dihydrogen phosphate.

The viscosity building agent can be one or more of a polyethylene glycol, a polyvinyl alcohol, a polyvinyl pyrrolidone, a polyvinyl alcohol, a methylcellulose, a hydroxyethylcellulose, a hydroxypropylcellulose, a guar gum, a hydroxypropyl guar gum, a gum arabic, a karaya gum, a xanthan gum, an agar, an alginic acid, a dextran, a heparin, a hyaluronic acid, a chondroitin sulfate, a starch, a chitin, a carrageenan, a polyacrylate, a casein, a gelatin, a collagen, a pectin, and an elastin.

The buffer can be on or more of a phosphate buffer, a citrate buffer, an acetate buffer, a carbonate buffer, a succinate buffer, a bicine buffer, a TRIS buffer, a tricine buffer, a TAPSO buffer, a HEPES buffer, a TES buffer, a MOPS buffer, a PIPES buffer, a cacodylate buffer, and a MES buffer.

The chelating agent can be one or more of a adeferoxamine, an ethylenediaminetetraacetic acid (EDTA), and an EGTA.

And the surfactant can be on or more of a sorbitan, a polysorbate, a poloxamer, a sodium lauryl sulfate, and a tyloxapol.

In some embodiments, the first ciprofloxacin composition may be used in methods of treating a bacterial infection in a subject in need thereof. Such methods involve the step of topically applying, at least once a day and to a body site of the subject, about 10 microliters or more of the first composition. In such methods, the application site is infected with a ciprofloxacin susceptible bacterium; and the application site can be one or more of a dermal surface, an ophthalmic surface, a mucosal surface, a fingernail surface, an ear canal, an oral cavity, a pharyngeal cavity, a nasal cavity, a pulmonary cavity, a vaginal cavity, and a rectal cavity.

In certain of such embodiments, the first composition possesses a more rapid onset of antibacterial activity against ciprofloxacin susceptible *Haemophilus* influenza, *Streptococcus pneumoniae*, *Escherichia coli*, *Staphylococcus aureus*, *Serrata marcescens*, and/or *Klebisiella pneumoniae* than the second pharmaceutical composition. And in certain of such embodiments, the more rapid onset of antibacterial activity comprises the first composition exhibiting, at a time within about 6 hours, preferably 3 hours, of starting a bacterial kill rate assay, a bacterial percentage log reduction in the kill rate assay that is at least 1.5-fold greater, 1.75-fold greater, or about 2-fold greater than the second composition.

BRIEF DESCRIPTION OF THE DRAWING

FIG. 1B is a *Haemophilus influenzae* percentage log reduction chart for ciprofloxacin formulations pH 4.5, 5.5, 6.5, and 7.5.

FIG. 3B is a *Streptococcus pneumoniae* percentage log reduction chart for ciprofloxacin formulations pH 4.5, 5.5, 6.5, and 7.5.

FIG. 7A is a *Klebisiella pneumoniae* time kill chart for ciprofloxacin formulations pH 4.5, 5.5, 6.5, and 7.5.

DETAILED DESCRIPTION OF THE INVENTION

Figure 1A:
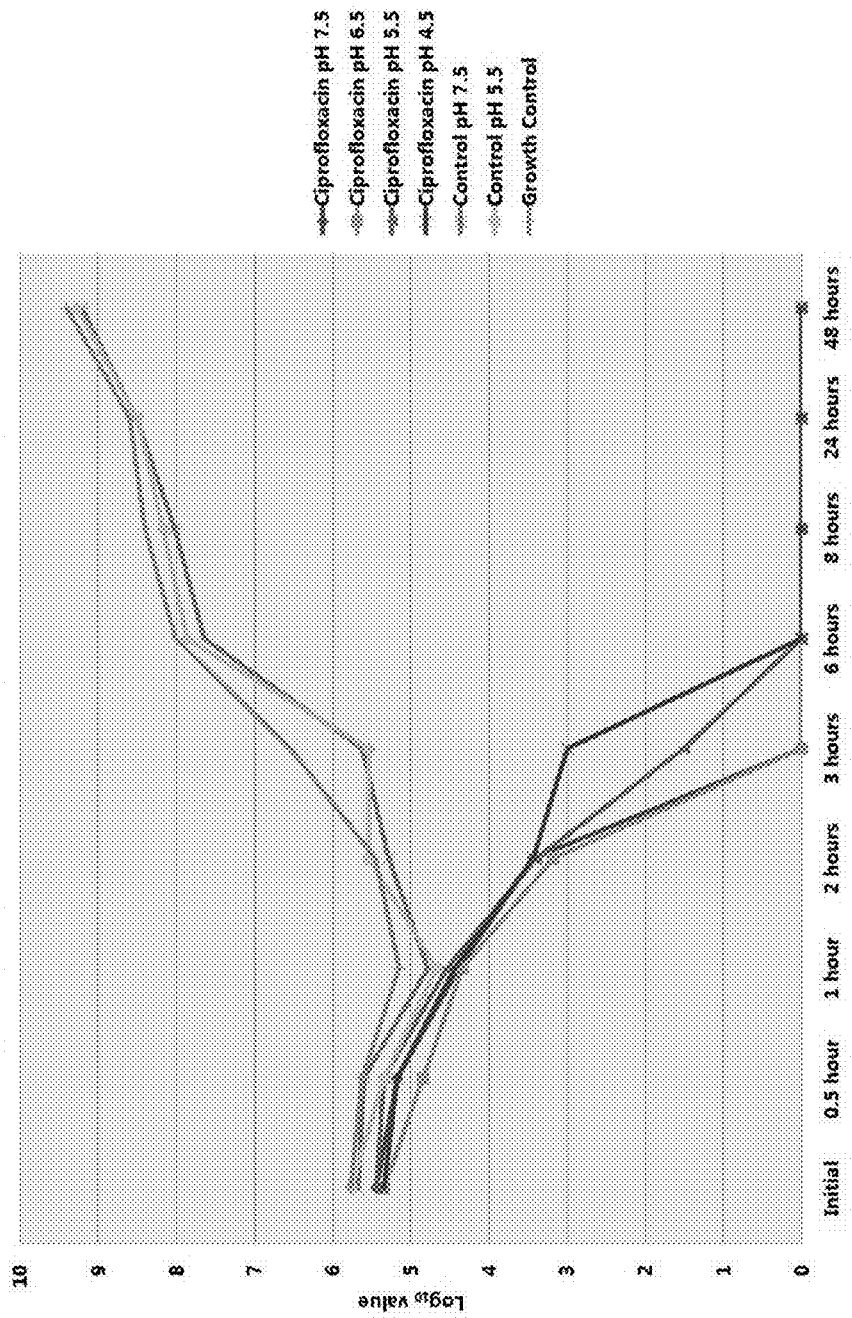
FIG. 1A is a *Haemophilus influenzae* time kill chart for ciprofloxacin formulations pH 4.5, 5.5, 6.5, and 7.5.

The quinolones are a group of antibacterial agents based on or resembling the 4-oxo-1, 4-dihydroquinoline skeleton. The first member of this group to be synthesized was nalidixic acid. Subsequently, a large number of quinolones have been synthesized, some of which have antibacterial potencies 1000 times greater than that of nalidixic acid and are active against both Gram-negative and Gram-positive organisms. Many such quinolones have a fluorine atom at position 6 of the quinolone structure (e.g. norfloxacin, ciprofloxacin, sparfloxacin), which significantly enhances antibacterial activity.

The major intracellular target of the quinolones is DNA gyrase, an essential bacterial enzyme which catalyzes the negative supercoiling of DNA in bacteria. In addition, gyrase can catalyze the relaxation of both negatively and positively supercoiled DNA, the unknotting of DNA, and the catenating or decatenating of doublestranded DNA circles. All of these gyrase-catalyzed reactions involve DNA breakage and strand-passage processes, and are sensitive to inhibition by quinolone interruption of the DNA breakage and ligation steps.

Gyrase consists of two subunits, A and B, of molecular weights 97 and 90 kDa respectively, and encoded by the gyrA and gyrB genes in *Escherichia coli*. The active gyrase enzyme is an $A_2B_2$ complex. The A subunits of gyrase are involved in the DNA breakage and ligation aspects of supercoiling, while the B subunits are responsible for ATP hydrolysis. (See, e.g., Maxwell, A. The molecular basis of quinolone action. *Journal of Antimicrobial Chemotherapy*. (1992) 30: 409-416.)

Without being bound to any particular theory, it is widely thought that quinolone mechanism of antibacterial action involves formation of a ternary complex composed of quinolone, gyrase, and DNA. This ternary complex is formed in a pocket of gyrA, referred to as the quinolone resistance determining-region (QRDR), wherein particular molecular groups/moieties of the quinolone interact with specific molecular groups/moeities of both the DNA and the gyrase to form the ternary complex. Gyrase crystal structure and structural modeling support this mechanism. In addition, the majority of mutations conferring resistance to quinolones destabilize/disrupt the ternary complex and arise within the quinolone resistance-determining region of GyrA, close to the active site where DNA is bound and cleaved by $Tyr^{122}$. Such mutations include GyrA ($Ser^{83} \rightarrow Trp$ or Leu), which gives 20-fold resistance to a wide range of quinolones. (See, e.g., Heddle, J and Maxwell, A. Quinolone-Binding Pocket of DNA Gyrase: Role of GyrB *Antimicrobial Agents and Chemotherapy*. (2002) 46:6, 1805-1815 and Barnard, F. and Maxwell, A. Interaction between DNA Gyrase and Quinolones: Effects of Alanine Mutations at GyrA Subunit Residues Ser and $Asp^{87}$. *Antimicrobial Agents and Chemotherapy*. (2001) 45:7, 1994-2000.)

United States Patent Application Publication No. 2009/0082337 (the '337 publication) discloses that quinolones typically have low solubility, and thus, extra measures have been used to increase their availability at the target sites. And it is known that ciprofloxacin exhibits significantly reduced water solubility at neutral pH, as compared to more acidic or more basic pH. (See, e.g., J. Bedard and L. E. Bryan, Interaction of the Fluoroquinolone Antimicrobial Agents Ciprofloxacin and Enoxacin with Liposomes. *Antimicrobial Agents and Chemotherapy*. (1989) 33:8, 1349-1382.) The '337 publication discloses quinolone compositions having a split pH range that avoids the reduced solubility pH range of the quinolones: i.e., pH 3.5 to 5.5 or pH 10.5 to 12.

U.S. Pat. No. 5,965,549 (the '549 patent) discloses aqueous formulations of ciprofloxacin in solution. The '549 patent discloses that water was the selected base for its formulations because it is not toxic, irritating, or sensitizing to the ear. The '549 patent discloses that its ciprofloxacin formulations desirably contain preservative to prevent microorganism contamination and to provide a reasonable shelf life. The preservative was required to be jointly soluble with ciprofloxacin in water over a common pH range. A requirement met with difficulty, at least partly inasmuch as ciprofloxacin solubility was determined to be limited to a narrow pH range. The '549 patent discloses that, in aqueous solutions containing from about 0.2 to about 1 weight percent ciprofloxacin HCl, precipitation was observed at pH above 5.5 at room temperature and pH above 5 at 5° C.

The '549 patent discloses that sodium benzoate, potassium sorbate, and benzyl alcohol were candidate preservatives for its ciprofloxacin formulations. The '549 patent discloses that sodium benzoate precipitated in 0.2 to 0.3 weight percent aqueous solutions thereof, at 5° C. and pH lower than about 4.5 to 5. Potassium sorbate precipitated in 0.1 to 0.15 weight percent aqueous solutions thereof, at 5° C. and pH lower than 4.5. And that benzyl alcohol has a solubility in aqueous solutions independent of pH.

The '549 patent discloses that, in view of the experimentally determined pH ranges for aqueous solubility of ciprofloxacin HCl and potassium sorbate, aqueous solutions containing them most preferably have a pH about 4.75. Further that, because the aqueous solubilities of ciprofloxacin hydrochloride and potassium sorbate are limited to a narrow mutual pH range, a buffering agent is desirable when potassium sorbate is used as a preservative in ciprofloxacin HCl solutions.

In regard to buffers, the '549 patent discloses that citrate buffer caused ciprofloxacin precipitation, and was unsuitable. But that acetate buffer was found effective at a concentration of 0.05 molar.

United States Patent Application No. 2007/0049552 (the '552 publication) discloses that ciprofloxacin is soluble in dilute (0.1N) hydrochloric acid and is practically insoluble in water and ethanol. The '552 patent discloses that, in order to achieve the 0.3% ciprofloxacin concentration necessary for therapeutic use in CILOXAN, an acidic buffer is employed at pH 4.5. And that, upon administration of CILOXAN to the eye, frequent burning and stinging sensation has been clinically reported due in part to the acidic formulation.

The '552 publication discloses that "[t]o avoid the development of resistance to topical antibiotics, high concentrations of a bactericidal drug with good solubility should be used at a dosing frequency that ensures that the drug concentrations are maintained above the $MIC_{90}$ of the suspected pathogens" (Steven J. Lichenstein, Contemporary Pediatrics, 2002, p 16-19). And that it is therefore desirable to have ciprofloxacin formulations of higher potency (greater than 0.3%) that will maintain concentrations of the drug higher than $MIC_{90}$. Such a formulation should increase therapeutic effectiveness, decrease the likelihood of formation of resistant strains of bacteria, decrease the duration of therapy and decrease the dosing regimen.

The '552 publication, however, discloses that current techniques do not provide a feasible way to produce such higher potency formulations because further reductions in pH would lead to even more serious side effects. And that fluoroquinolone solutions, such as ciprofloxacin solutions, are stable at acidic pH (<5), but considerable degradation occurs at higher pH.

The '552 publication discloses high potency, aqueous pharmaceutical compositions of fluoroquinolone antibiotic (e.g., ciprofloxacin). The ciprofloxacin is complexed with a cyclodextrin (e.g., sulfobutylether7-β-cyclodextrin) in the presence of a hydroxy acid (e.g., citric acid) in water. And the compositions contain ciprofloxacin in an amount from 1 mg/ml to 100 mg/ml.

U.S. Pat. No. 5,023,257 (the '257 patent) discloses intramuscular injection forms which contain, as the active compound, gyrase inhibitors from the group comprising quinolone- and 1,8-naphthyridone-3-carboxylic acids. The '257 patent discloses that ciprofloxacin solutions of up to 5% strength for intramuscular administration are very poorly tolerated because of their non-physiological pH in the acid or alkaline range. After intramuscular injection of aqueous acid or alkaline solutions, considerable intolerances and damage up to necroses have been found in the muscular tissue.

The '257 patent discloses it found that ciprofloxacin is well tolerated following intramuscular administration if administered in the form of an aqueous suspension of the betaine form having an approximate neutral pH value. And further that aqueous ciprofloxacin suspensions that contain the active compound in the betaine form ensure protracted release of the active compound.

Embodiments of the present invention provide aqueous ciprofloxacin compositions that have a pH of more than or about 5.5, 5.6, 5.7, 5.75, 5.8, 5.9, or 6; about 6.5, 7, 8, 8.5, or 9; less than or about 10; or a range therebetween. Such ciprofloxacin compositions possess a significant percentage of their total ciprofloxacin content in suspended form. Such ciprofloxacin formulations possess an unexpectedly advantageous rapid onset of antibacterial activity in comparison to conventional ciprofloxacin compositions having relatively lower pH, such as pH 4.5. And such ciprofloxacin compositions are suitable for topical application to a variety of target body sites of a subject in need thereof, advantageously providing reduced irritation and/or heightened comfort potential.

Examples of ophthalmic conditions that may be treated with the ciprofloxacin compositions of the present invention include conjunctivitis, keratitis, blepharitis, dacryocystitis, hordeolum and corneal ulcers. In addition, ciprofloxacin compositions of the invention may be used prophylactically in connection with various ophthalmic surgical procedures that create a risk of bacterial infection.

Examples of otic conditions that may be treated with the ciprofloxacin compositions of the present invention include otitis externa and otitis media resulting from gram-positive and/or gram negative bacteria susceptible to ciprofloxacin. With respect to the treatment of otitis media, the ciprofloxacin compositions of the present invention are useful in cases where the tympanic membrane has ruptured or tympanostomy tubes have been implanted. In addition, the ciprofloxacin compositions may be used prophylactically in connection with various otic surgical procedures that create a risk of bacterial infection.

Examples of nasal conditions that may be treated with the ciprofloxacin compositions of the present invention include sinusitis resulting from gram-positive and/or gram negative bacteria susceptible to ciprofloxacin. In addition, the ciprofloxacin compositions may be used prophylactically in connection with various nasal surgical procedures that create a risk of bacterial infection.

Examples of pulmonary conditions that may be treated with the ciprofloxacin compositions of the present invention include respiratory tract infections resulting from gram-positive and/or gram negative bacteria susceptible to ciprofloxacin. In addition, the ciprofloxacin compositions may be used prophylactically in connection with various pulmonary surgical procedures that create a risk of bacterial infection.

Examples of dermal conditions that may be treated with the ciprofloxacin compositions of the present invention include impetigo, cellulitis, pustules, furuncles, chancres, erysipelas, aquarium granuloma, and bacterial ulcer resulting from gram-positive and/or gram negative bacteria susceptible to ciprofloxacin. In addition, the ciprofloxacin compositions may be used prophylactically in connection with scrapes, cuts, bites, and the like that that create a risk of bacterial infection.

Examples of vaginal conditions that may be treated with the ciprofloxacin compositions of the present invention include bacterial vaginosis resulting from gram-positive and/or gram negative bacteria susceptible to ciprofloxacin.

Examples of rectal conditions that may be treated with the ciprofloxacin compositions of the present invention include proctitis resulting from gram-positive and/or gram negative bacteria susceptible to ciprofloxacin.

In certain embodiments, the ciprofloxacin compositions of the present invention are isotonic, mildly hypotonic, or mildly hypertonic to the tissues upon which they are topically applied. The tonicity of ciprofloxacin compositions according to such embodiments can be about 100 mOsm, about 150 mOsm, about 200 mOsm, about 250 mOsm, about 300 mOsm, about 350 mOsm, about 400 mOsm, about 450 mOsm, about 500 mOsm, about 550 mOsm, about 600 mOsm, or a range therebetween. Osmolality adjusting agents (sometimes referred to as tonicity agents) may be included in the ciprofloxacin compositions in any amount needed to achieve such tonicities, including without limitation glycerol, mannitol, xylitol, sorbitol, dextrose, glucose, maltose, trehalose, sucrose, cyclodextrin, propylene glycol, sodium chloride, potassium chloride, calcium chloride, magnesium chloride, sodium bisulfite, sodium sulfite, sodium sulfate, sodium bicarbonate, sodium carbonate, sodium thiosulfate, potassium acetate, sodium acetate, magnesium sulfate, disodium hydrogen phosphate, sodium dihydrogen phosphate, potassium dihydrogen phosphate, or combinations thereof. Ciprofloxacin compositions of the invention can contain, by weight of the finished formulation, osmolality adjusting agents in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, about 6%, about 7%, about 8%, about 9%, about 10%, or a range therebetween.

In certain embodiments, the viscosity of ciprofloxacin compositions of the invention are increased above that of simple aqueous formulations to achieve, without limitation, increased tissue adherence of the formulation, decreased variability in dispensing the formulation, decreased physical separation of suspended components of the formulation, or combinations thereof. The viscosity of such ciprofloxacin compositions can be adjusted with viscosity building agents including, without limitation, polyethylene glycol, polyvinyl alcohol, polyvinyl pyrrolidone, polyvinyl alcohol, methylcellulose, hydroxypropylmethylcellulose, hydroxyethylcellulose, carboxymethylcellulose, hydroxypropylcellulose, guar gum, hydroxypropyl guar gum, gum arabic; karaya gum, xanthan gum, agar, alginic acid, cyclodextrin, dextran, heparin, hyaluronic acid, chondroitin sulfate, starch, chitin, carrageenan, polyacrylates, methyl polyacrylates, amine polyacrylates, ammonium polyacrylates, casein, gelatin, collagen, pectin, elastin, and combinations thereof. Ciprofloxacin compositions of the invention can contain, by weight of the finished formulation, viscosity building agents in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, about 6%, about 7%, about 8%, about 9%, about 10%, or a range therebetween.

Ciprofloxacin compositions according to the present invention have a pH in a range of from about 6 to about 8, and in some embodiments in a range of from about 6.5 to about 7.5. Ciprofloxacin compositions can be pH adjusted as needed by adding appropriate amounts of a pH adjusting agent(s), including without limitation, hydrochloric acid, sulfuric acid, phosphoric acid, sodium hydroxide, potassium hydroxide, calcium hydroxide, magnesium hydroxide, triethanolamine, monoethanolamine, and/or diisopropanolamine. Ciprofloxacin compositions can be pH maintained as needed by adding appropriate amounts of a variety of buffers including, without limitation, phosphate buffer, citrate buffer, acetate buffer, carbonate buffer, succinate buffer, bicine buffer, TRIS buffer, tricine buffer, TAPSO buffer, HEPES, TES buffer, MOPS buffer, PIPES buffer, cacodylate buffer, MES buffer, or combinations thereof. Ciprofloxacin compositions of the invention can contain, by weight of the finished formulation, pH adjusting agents and/or buffers in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, about 6%, about 7%, about 8%, about 9%, about 10%, or a range therebetween.

In some embodiments, ciprofloxacin compositions according to the present invention contain chelating agent(s) and/or preservative(s). Exemplary chelating agent(s) suitable for use in such ciprofloxacin compositions include, without limitation, deferoxamine (DEF), EDTA EGTA, and combinations thereof. Exemplary preservative(s) suitable for use in such ciprofloxacin compositions include, without limitation, benzalkonium chloride, thimerosal, chlorobutanol, methyl paraben, propyl paraben, phenylethyl alcohol, borates, sorbates, and combinations thereof. Ciprofloxacin compositions of the invention can contain, by weight of the finished formulation, chelating agents in amounts of about 0.001%, about 0.005%, about 0.01%, about 0.05%, about 0.1%, about 0.5%, about 1%, about 125%, about 1.5%, about 1.75%, about 2%, about 2.5%, about 3%, about 3.5%, about 4%, about 4.5%, about 5%, or a range therebetween.

In some embodiments, ciprofloxacin compositions according to the present invention contain surfactants to stabilize suspensions, increase uniformity in dispensing the formulation, and/or promote tissue adherence of the formulation. Exemplary surfactants suitable for use in such ciprofloxacin compositions include, without limitation, sorbitan monooleate (Span 80) and sorbitan monostearate (Span 60); polysorbate 20, 60, and 80; pluronic F-68, F-84, F-127, and P-103; sodium lauryl sulfate; tyloxopol; and combinations thereof. Ciprofloxacin compositions of the invention can contain, by weight of the finished formulation, surfactants in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, or a range therebetween.

Bacterial infections are often attended by inflammation, pain, congestion, or combinations thereof. Similar attendant symptoms are often associated with, ophthalmic, otic, and nasal surgical procedures that create a risk of bacterial infections. In addition, sinusitis can involve nasal polyps associated with fungal pathogens. Accordingly, certain embodiments of the present invention provide ciprofloxacin compositions that further include at least one additional drug. Exemplary, non-limiting, classes of such additional drug(s) are anti-inflammatories, decongestants, topical anesthetics, and antifungals.

Anti-inflammatory drugs suitable for use in ciprofloxacin compositions according to the present invention include, without limitation, cortisone, desoxycorticosone, hydrocortisone, methylprednisolone, prednisone, prednisolone, triamcinolone, dexamethasone, betamethasone, beclomethasone, beclomethasone-17,21-dipropionate, budesonide, flunisolide, fludrocortisone, mometasone, fluticasone, alclometasone, clocortolone, flurandrenolide, fluocinonide, hydrocortisone acetate, fluorometholone, fluocinolone acetonide, diflucortolone valerate, paramethasone acetate, halcinonide, hydrocortisone phosphate, clobetasone butyrate, amcinonide, prednisolone succinate, and combinations thereof. Ciprofloxacin compositions of the invention can contain, by weight of the finished formulation, corticosteroids in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, or a range therebetween.

Non-steroidal anti-inflammatory drugs (NSAIDS) that may be used to carry out the present invention include, without limitation, aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, as well as COX-2 inhibitors such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and combinations thereof. Ciprofloxacin compositions of the invention can contain, by weight of the finished formulation, NSAIDS in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, or a range therebetween.

Decongestant drugs that may be used to carry out the present invention include, without limitation, α-adrenergic agonists such as epinephrine, ephedrine, oxymetazoline, tetrahydrozoline, naphazoline, phenylephrine, methylephedrine, and combinations thereof. Ciprofloxacin compositions of the invention can contain, by weight of the finished formulation, decongestants in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, or a range therebetween.

Topical anesthetic drugs suitable for use in ciprofloxacin compositions according to the present invention include, without limitation, lidocaine, tetracaine, benzocaine, procaine, mepivacaine, bupivacaine, etidocaine, cocaine, and combinations thereof. Ciprofloxacin formulations of the invention can contain, by weight of the finished formulation, topical anesthetics in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, or a range therebetween.

Antifungal drugs suitable for use in ciprofloxacin compositions according to the present invention include, without limitation, bifonazole, butoconazole, clotrimazole, econazole, fenticonazole, fluconazole, flutrimazole, isoconazole, itraconazole, ketoconazole, miconazole, omoconazole, oxiconazole, parconazole, sertaconazole, sulconazole, tioconazole, voriconazole, a mphotericin B, flucytosine, griseofulvin, nikkomycin, nystatin, potassium iodide, sordarin, undecylenic acid, and combinations thereof. Ciprofloxacin formulations of the invention can contain, by weight of the finished formulation, pH adjusting agents and/or buffers in amounts of about 0.001%, about 0.005%, about 0.01%, about 0.05%, about 0.1%, about 0.5%, about 1%, about 1.25%, about 1.5%, about 1.75%, about 2%, about 2.5%, about 3%, about 3.5%, about 4%, about 4.5%, about 5%, or a range therebetween.

The ciprofloxacin compositions of the invention can be topically applied to bacterially infected ophthalmic, otic, nasal, and pulmonary tissues as a single dosage, or as a plurality of dosages. For example, the ciprofloxacin compositions may be administered in some embodiments once per day, or twice per day, three times per day, four times per day, five times per day, six times per day, seven time per day, or eight times per day, either in temporally evenly spaced applications or in clustered applications, for example clustered in one, two, three, or four dosages of morning and evening applications, or morning, noon, and evening applications. As will be understood, an effective amount of aqueous ciprofloxacin formulation will vary depending upon the particular use, the particular patient, tissue, and bacterial infection for which the formulation is being applied.

EXAMPLE 1

Bacterial Kill Rate Assays

Bacterial kill rate assays were conducted on gram positive and gram negative species for ciprofloxacin formulations pH 4.5, 5.5, 65, and 7.5. The gram positive bacteria were *Staphylococcus aureus* (ATCC 29213) and *Streptococcus pneumonia* (ATCC 700902). The gram negative bacteria were *Moraxella catarrhalis* (ATCC 25238), *Escherichia coli* (ATCC 25922), *Klebsiella pneumonia* (ATCC 700603), *Serratia marcescens* (ATCC 14041), and *Haemophilus influenza* (ATCC 49247). The ciprofloxacin formulations are shown in Table 1.

TABLE 1

| Ingredient | Ciprofloxacin pH 4.5* | Ciprofloxacin pH 5.5 | Ciprofloxacin pH 6.5 | Ciprofloxacin pH 7.5 |
| --- | --- | --- | --- | --- |
| Ciprofloxacin HCl monohydrate | 0.35% w/w | 0.35% w/w | 0.35% w/w | 0.35% w/w |
| Dexamethasone alcohol | 0.1% w/w | 0.1% w/w | 0.1% w/w | 0.1% w/w |
| Hydroxyethylcellulose | 0.2% w/w | 0.2% w/w | 0.2% w/w | 0.2% w/w |
| Benzalkonium chloride | 0.01% w/w | 0.01% w/w | 0.01% w/w | 0.01% w/w |
| Sodium acetate | 0.03% w/w | 0.03% w/w | 0.03% w/w | 0.03% w/w |
| Acetic acid | 0.04% w/w | 0.04% w/w | 0.04% w/w | 0.04% w/w |
| Sodium chloride | 0.53% w/w | 0.53% w/w | 0.53% w/w | 0.53% w/w |
| Disodium edetate | 0.01% w/w | 0.01% w/w | 0.01% w/w | 0.01% w/w |
| Tyloxapol | 0.05% w/w | 0.05% w/w | 0.05% w/w | 0.05% w/w |
| Boric acid | 0.06% w/w | 0.06% w/w | 0.06% w/w | 0.06% w/w |
| Sodium hydroxide | q.s. to pH 4.5 | q.s. to pH 5.5 | q.s. to pH 6.5 | q.s. to pH 7.5 |
| Water | q.s. to 100% w/w | q.s. to 100% w/w* | q.s. to 100% w/w* | q.s. to 100% w/w* |

*Note that that the ciprofloxacin pH 4.5 formulation was commercially available and purchased, and the ciprofloxacin pH 5.5, 6.5, and 7.5 formulations were prepared therefrom by adding small amounts of NaOH to adjust pH. The above-listed composition of the Ciprofloxacin pH 4.5 was derived from experimental studies and published information.

Bacteria Preparation.

A stock of each bacteria studied was plated onto pH 7.2-7.3 tryptic soy agar plate containing per liter: 17 g casein pancreatic digest, 3 g soybean meal papaic digest, 5 g sodium chloride, 2.5 g dibasic potassium phosphate, 2.5 g glucose monohydrate, and 15 g agar; and incubated at 37° C. Two or three bacterial colonies were picked from the plates following 20+ hours outgrowth at 37° C., and inoculated into pre-warmed (37° C.), pH 7.2-7.45 cation-adjusted Mueller-Hinton broth ("CAMHβ") containing per liter: 3 g beef extract, 17.5 g casein acid lysate, and 1.5 g starch. This inoculate was incubated overnight at 37° C. with agitation, diluted 1/2500 in pre-warmed CAMHβ, and then cultured at 37° C. with agitation. Samples were taken from this bacterial culture until a 0.1 absorbance measurement was obtained with a spectrophotometer using a wavelength of 450 nm and a 19 mm diameter spectrophotometer tube. From this culture was prepared a bacterial inoculum possessing $1 \times 10^8$ cfu/ml CAMHβ. 200 μls of this bacterial inoculum were aliquoted into vessels containing 20 ml cation-adjusted Mueller-Hinton broth.

Time Kill Experiments.

100 μl of the ciprofloxacin pH 4.5, 5.5, 6.5, or 7.5 formulations were added to independent bacterial inoculum aliquots. One of the bacterial inoculum aliquots was pH adjusted to 5.5 to form the pH 5.5 control. And one of the bacterial inoculum aliquots was pH adjusted to 7.5 to form the pH 7.5 control. The growth control was formed straight from one of the bacterial inoculum aliquots. Each of these test and control bacterial preparations were incubated at 37° C., for 48 hours and with agitation.

In the course of the 48 hour incubation, 500 μl samples were taken at initial (less than 5 minutes), 0.5 hour, 1 hour, 2 hour, 3 hour, 6 hour, 8 hour, 24 hour, and 48 hour time points. Each of those samples were pelleted by centrifugation and resuspended in 500 μl saline solution. 20 μl of the resuspended samples were plated onto soya bean casein digest agar plates and incubated for 24 hours at 37° C. Bacterial colonies on the plates were counted and recorded as raw cfu/plate. The raw cfu/plate numbers were multiplied by the appropriate dilution factors to determine raw surviving bacteria numbers for each time point. The raw surviving bacteria numbers were converted to $log_{10}$ values. And Percentage $log_{10}$ reduction values were calculated with the following formula.

$$\text{Percentage } log_{10} \text{ reduction} = (\text{initial } log_{10} \text{ value} - \text{time interval } log_{10} \text{ value})/\text{initial } log_{10} \text{ value}) \times 100.$$

EXAMPLE 2

*Haemophilus influenzae*

A time kill study for *Haemophilus influenzae* was conducted according to the protocol described in Example 1. The $log_{10}$ values and the percentage log reduction values for this time kill study are set forth in Tables 2 and 3, respectively.

TABLE 2

Log$_{10}$ values for *Haemophilus* Influenzae time kill study

| Time | Ciprofloxacin pH 7.5 | Ciprofloxacin pH 6.5 | Ciprofloxacin pH 5.5 | Ciprofloxacin pH 4.5 | Control pH 7.5 | Control pH 5.5 | Growth Control |
|---|---|---|---|---|---|---|---|
| Initial | 5.44 | 5.35 | 5.44 | 5.35 | 5.68 | 5.76 | 5.78 |
| 0.5 hour | 5.18 | 4.85 | 5.35 | 5.18 | 5.61 | 5.35 | 5.63 |
| 1 hour | 4.39 | 4.35 | 4.54 | 4.44 | 4.78 | 4.68 | 5.15 |
| 2 hours | 3.44 | 3.18 | 3.4 | 3.44 | 5.29 | 5.54 | 5.46 |
| 3 hours | 0 | 0 | 1.5 | 3 | 5.63 | 5.54 | 6.54 |
| 6 hours | 0 | 0 | 0 | 0 | 7.65 | 7.87 | 8.01 |
| 8 hours | 0 | 0 | 0 | 0 | 8.03 | 8.17 | 8.4 |
| 24 hours | 0 | 0 | 0 | 0 | 8.51 | 8.5 | 8.6 |
| 48 hours | 0 | 0 | 0 | 0 | 9.21 | 9.28 | 9.41 |

TABLE 3

Percentage log reduction values for *Haemophilus Influenzae* time kill study

| Time | Ciprofloxacin pH 7.5 | Ciprofloxacin pH 6.5 | Ciprofloxacin pH 5.5 | Ciprofloxacin pH 4.5 |
|---|---|---|---|---|
| 0.5 hour | 4.8 | 9.3 | 1.6 | 3.2 |
| 1 hour | 19.3 | 18.7 | 16.5 | 17 |
| 2 hours | 36.8 | 40.6 | 37.5 | 35.7 |
| 3 hours | 100 | 100 | 72.4 | 43.9 |
| 6 hours | 100 | 100 | 100 | 100 |
| 8 hours | 100 | 100 | 100 | 100 |
| 24 hours | 100 | 100 | 100 | 100 |
| 48 hours | 100 | 100 | 100 | 100 |

The *Haemophilus influenzae* time kill log$_{10}$ values and percentage reduction values are plotted as a function of time in FIG. 1A and FIG. 1B, respectively.

EXAMPLE 3

*Moraxella catarrhaliss*

A time kill study for *Moraxella catarrhaliss* was conducted according to the protocol described in Example 1. The log$_{10}$ values and the percentage log reduction values for this time kill study are set forth in Tables 4 and 5, respectively.

TABLE 4

Log$_{10}$ values for *Moraxella catarrhaliss* time kill study

| Time | Ciprofloxacin pH 7.5 | Ciprofloxacin pH 6.5 | Ciprofloxacin pH 5.5 | Ciprofloxacin pH 4.5 | Control pH 7.5 | Control pH 5.5 | Growth Control |
|---|---|---|---|---|---|---|---|
| Initial | 4.72 | 4.72 | 4.67 | 4.45 | 5.28 | 5.28 | 5.16 |
| 0.5 hour | 4.54 | 4.39 | 4.29 | 4.35 | 5.39 | 5.13 | 5.26 |
| 1 hour | 4.15 | 4.21 | 4.24 | 4.18 | 5.24 | 5.18 | 5.35 |
| 2 hours | 3.71 | 3.62 | 3.54 | 2.85 | 5.45 | 5.36 | 5.8 |
| 3 hours | 0 | 0 | 0 | 0 | 5.84 | 5.59 | 6.1 |
| 6 hours | 0 | 0 | 0 | 0 | 6.76 | 6.35 | 7.33 |
| 8 hours | 0 | 0 | 0 | 0 | 7.63 | 7.54 | 7.85 |
| 24 hours | 0 | 0 | 0 | 0 | 8.93 | 8.87 | 9.19 |
| 48 hours | 0 | 0 | 0 | 0 | 9.4 | 9.34 | 9.47 |

TABLE 5

Percentage log reduction values for *Moraxella catarrhaliss* time kill study

| Time | Ciprofloxacin pH 7.5 | Ciprofloxacin pH 6.5 | Ciprofloxacin pH 5.5 | Ciprofloxacin pH 4.5 |
|---|---|---|---|---|
| 0.5 hour | 3.7 | 7 | 8.2 | 2.3 |
| 1 hour | 11.3 | 10.8 | 9.2 | 6 |
| 2 hours | 20.6 | 23.3 | 24.2 | 36 |
| 3 hours | 100 | 100 | 100 | 100 |
| 6 hours | 100 | 100 | 100 | 100 |
| 8 hours | 100 | 100 | 100 | 100 |
| 24 hours | 100 | 100 | 100 | 100 |
| 48 hours | 100 | 100 | 100 | 100 |

Figure 2A:
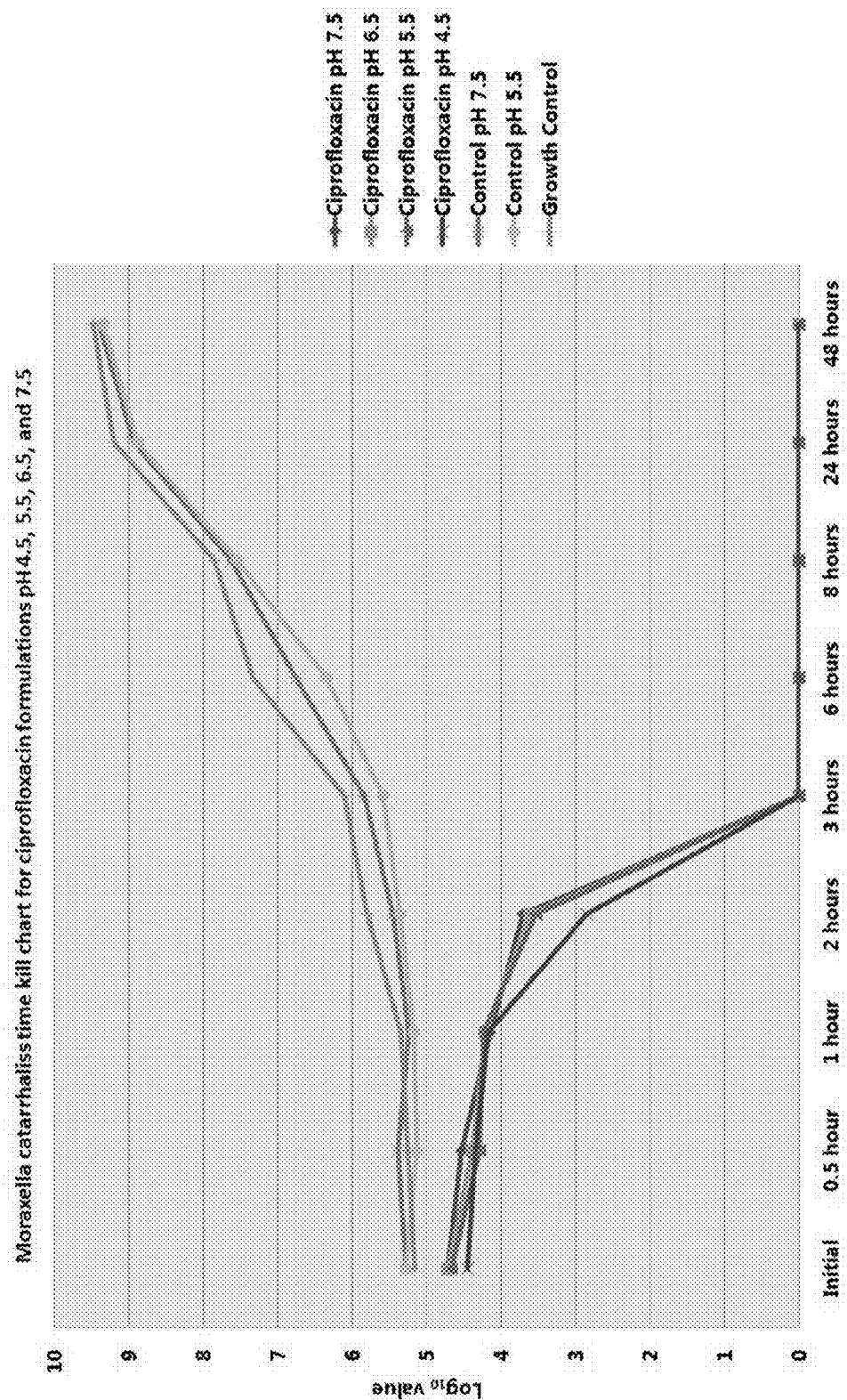
FIG. 2A is a *Moraxella catarrhaliss* time kill chart for ciprofloxacin formulations pH 4.5, 5.5, 6.5, and 7.5.
Figure 2B:
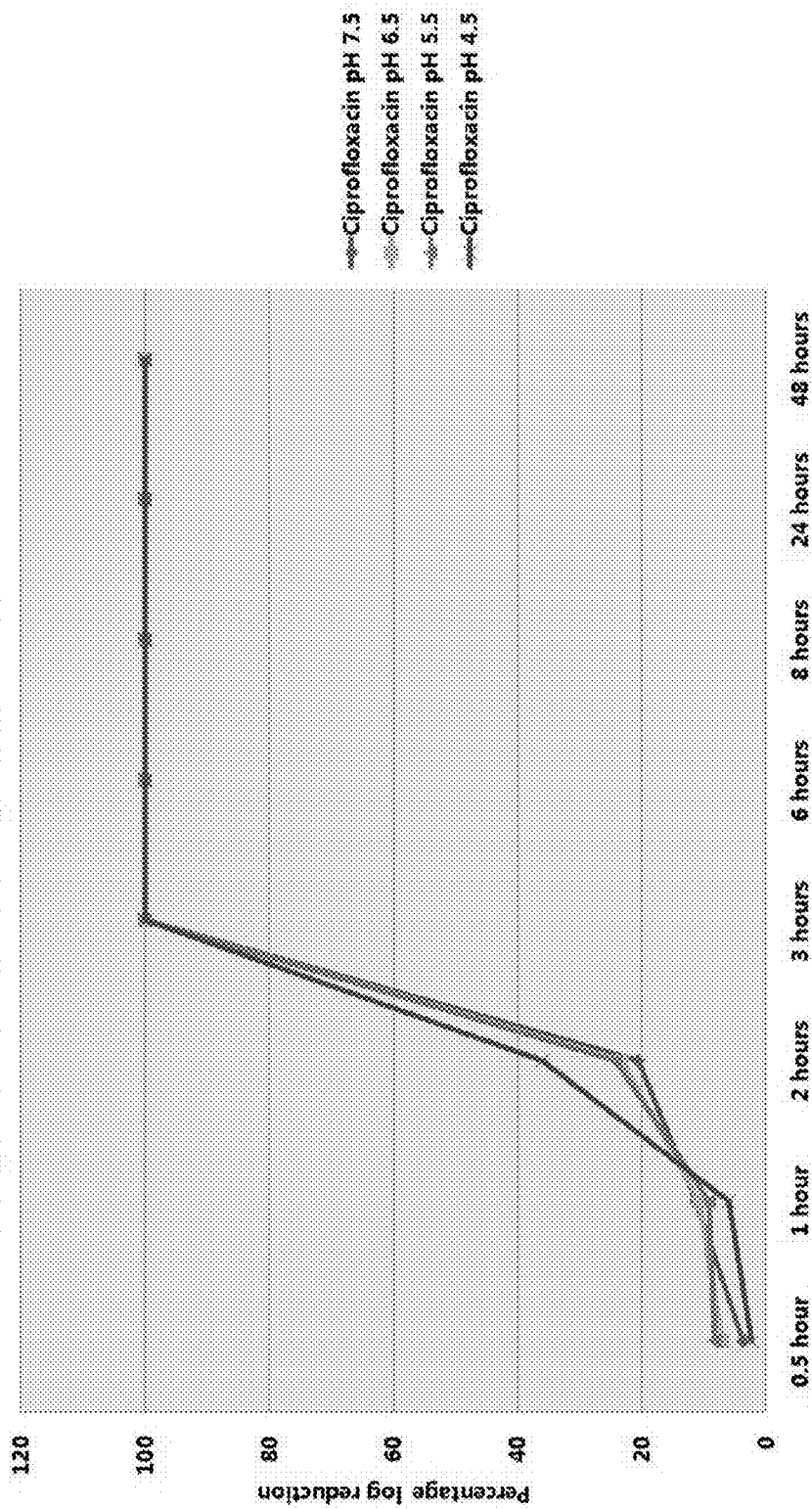
FIG. 2B is a *Moraxella catarrhaliss* percentage log reduction chart for ciprofloxacin formulations pH 4.5, 5.5, 6.5, and 7.5.

The *Moraxella catarrhaliss* time kill log$_{10}$ values and percentage reduction values are plotted as function of time in FIG. 2A and FIG. 2B, respectively.

EXAMPLE 4

*Streptococcus pneumoniae*

A time kill study for *Streptococcus pneumoniae* was conducted according to the protocol described in Example 1. The log$_{10}$ values and the percentage log reduction values for this time kill study are set forth in Tables 6 and 7, respectively.

TABLE 6

Log$_{10}$ values for *Streptococcus pneumoniae* time kill study

| Time | Ciprofloxacin pH 7.5 | Ciprofloxacin pH 6.5 | Ciprofloxacin pH 5.5 | Ciprofloxacin pH 4.5 | Control pH 7.5 | Control pH 5.5 | Growth Control |
|---|---|---|---|---|---|---|---|
| Initial | 4.81 | 4.44 | 4.6 | 4.74 | 4.9 | 4.81 | 5.05 |
| 0.5 hour | 4.74 | 4 | 4.35 | 4.09 | 4.92 | 4.81 | 4.97 |
| 1 hour | 3.76 | 3.86 | 3.94 | 4.03 | 5.22 | 5.08 | 5.4 |
| 2 hours | 3.35 | 3 | 3.51 | 3.29 | 5.78 | 5.45 | 5.79 |
| 3 hours | 0 | 1.35 | 1.5 | 3.35 | 6.54 | 6.35 | 6.47 |
| 6 hours | 0 | 0 | 0 | 0 | 7.68 | 7.61 | 7.82 |
| 8 hours | 0 | 0 | 0 | 0 | 8.13 | 8.28 | 8.3 |
| 24 hours | 0 | 0 | 0 | 0 | 6.07 | 6.23 | 6.27 |
| 48 hours | 0 | 0 | 0 | 0 | 5.05 | 5.14 | 5.31 |

TABLE 7

Percentage log reduction values for *Streptococcus pneumoniae* time kill study

| Time | Ciprofloxacin pH 7.5 | Ciprofloxacin pH 6.5 | Ciprofloxacin pH 5.5 | Ciprofloxacin pH 4.5 |
|---|---|---|---|---|
| 0.5 hour | 1.5 | 9.9 | 5.4 | 13.7 |
| 1 hour | 18.3 | 13 | 14.3 | 14.9 |
| 2 hours | 27.2 | 32.4 | 23.7 | 30.6 |
| 3 hours | 100 | 69.6 | 67.4 | 29.3 |
| 6 hours | 100 | 100 | 100 | 100 |
| 8 hours | 100 | 100 | 100 | 100 |
| 24 hours | 100 | 100 | 100 | 100 |
| 48 hours | 100 | 100 | 100 | 100 |

Figure 3A:
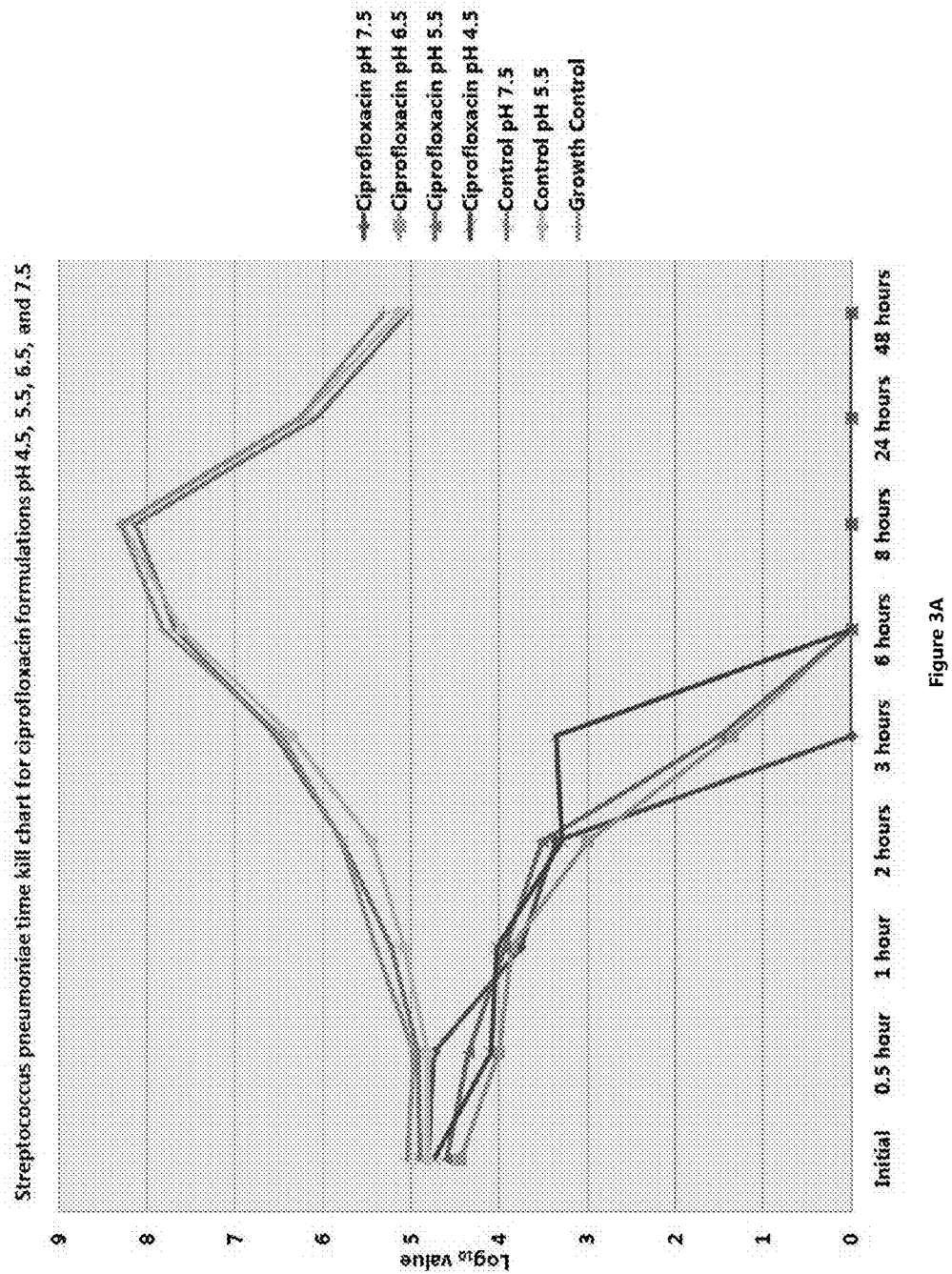
FIG. 3A is a *Streptococcus pneumoniae* time kill chart for ciprofloxacin formulations pH 4.5, 5.5, 6.5, and 7.5.

The *Streptococcus pneumoniae* time kill log$_{10}$ values and percentage reduction values are plotted as function of time in FIG. 3A and FIG. 3B, respectively.

EXAMPLE 5

*Escherichia coli*

A time kill study for *Escherichia coli* was conducted according to the protocol described in Example 1. The log$_{10}$ values and the percentage log reduction values for this time kill study are set forth in Tables 8 and 9, respectively.

TABLE 8

Log$_{10}$ values for *Escherichia coli* time kill study

| Time | Ciprofloxacin pH 7.5 | Ciprofloxacin pH 6.5 | Ciprofloxacin pH 5.5 | Ciprofloxacin pH 4.5 | Control pH 7.5 | Control pH 5.5 | Growth Control |
|---|---|---|---|---|---|---|---|
| Initial | 3.86 | 3.9 | 3.87 | 3.89 | 5.39 | 5.24 | 5.4 |
| 0.5 hour | 2.94 | 3.09 | 3.39 | 3.42 | 5.35 | 5.35 | 5.47 |
| 1 hour | 2.7 | 1.59 | 3.33 | 3.24 | 5.7 | 5.74 | 6.08 |
| 2 hours | 1.35 | 1.59 | 1.35 | 2.7 | 6.72 | 6.89 | 7.09 |
| 3 hours | 0 | 0 | 0 | 0 | 7.67 | 7.77 | 7.99 |
| 6 hours | 0 | 0 | 0 | 0 | 8 | 8.18 | 8.26 |
| 8 hours | 0 | 0 | 0 | 0 | 8.3 | 8.45 | 8.51 |
| 24 hours | 0 | 0 | 0 | 0 | 8.93 | 9.04 | 9.36 |
| 48 hours | 0 | 0 | 0 | 0 | 8.04 | 8.1 | 8.3 |

TABLE 9

Percentage log reduction values for *Escherichia coli* time kill study

| Time | Ciprofloxacin pH 7.5 | Ciprofloxacin pH 6.5 | Ciprofloxacin pH 5.5 | Ciprofloxacin pH 4.5 |
|---|---|---|---|---|
| 0.5 hour | 23.9 | 20.9 | 12.5 | 12 |
| 1 hour | 30.3 | 59.3 | 14.1 | 16.7 |
| 2 hours | 65.2 | 59.3 | 65.2 | 30.6 |
| 3 hours | 100 | 100 | 100 | 100 |
| 6 hours | 100 | 100 | 100 | 100 |
| 8 hours | 100 | 100 | 100 | 100 |
| 24 hours | 100 | 100 | 100 | 100 |
| 48 hours | 100 | 100 | 100 | 100 |

Figure 4A:
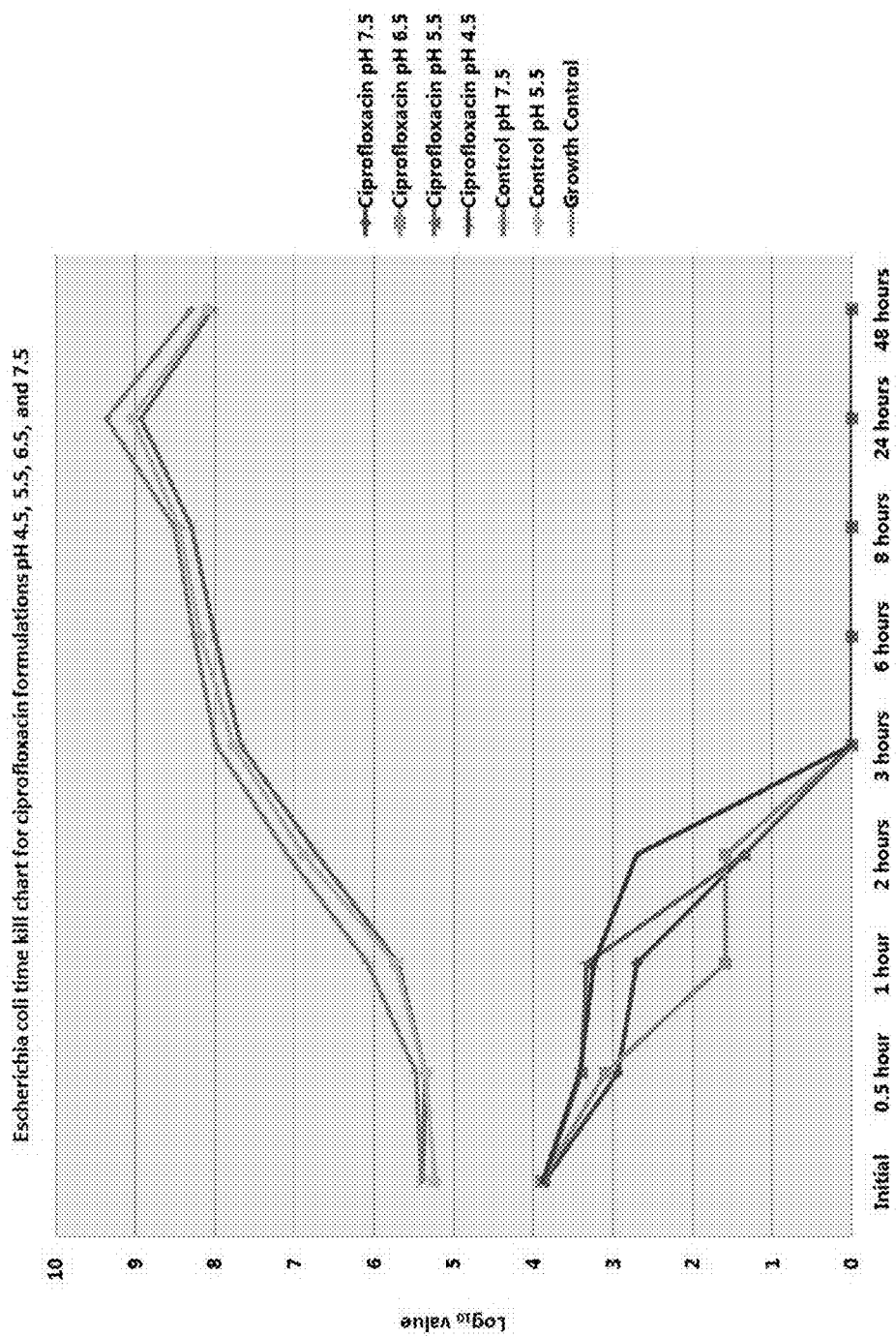
FIG. 4A is an *Escherichia coli* time kill chart for ciprofloxacin formulations pH 4.5, 5.5, 6.5, and 7.5.
Figure 4B:
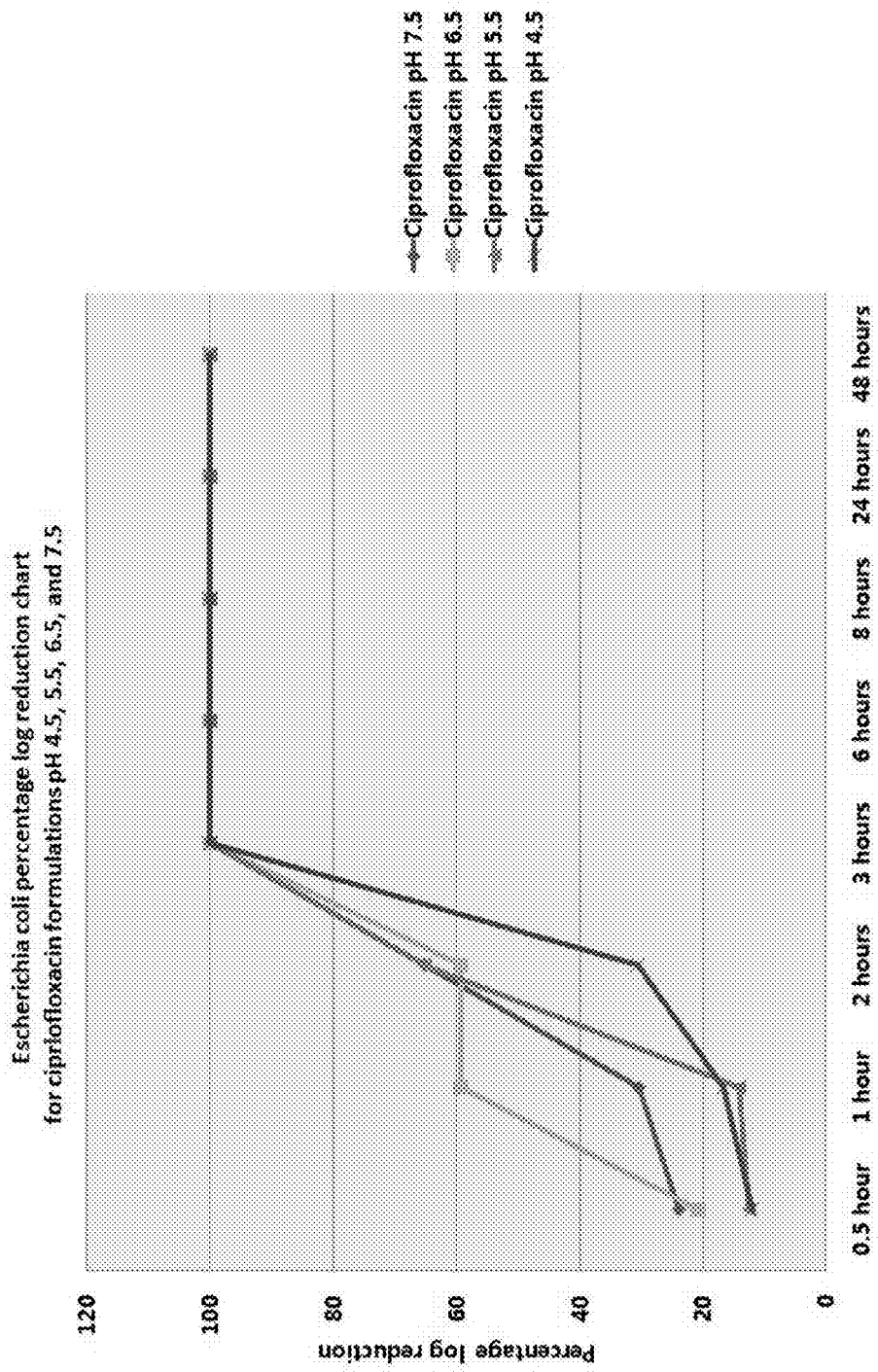
FIG. 4B is an *Escherichia coli* percentage log reduction chart for ciprofloxacin formulations pH 4.5, 5.5, 6.5, and 7.5.

The *Escherichia coli* time kill log$_{10}$ values and percentage reduction values are plotted as function of time in FIG. 4A and FIG. 4B, respectively.

EXAMPLE 6

*Staphylococcus aureus*

A time kill study for *Staphylococcus aureus* was conducted according to the protocol described in Example 1. The log$_{10}$ values and the percentage log reduction values for this time kill study are set forth in Tables 10 and 11, respectively.

TABLE 10

Log$_{10}$ values for *Staphylococcus aureus* time kill study

| Time | Ciprofloxacin pH 7.5 | Ciprofloxacin pH 6.5 | Ciprofloxacin pH 5.5 | Ciprofloxacin pH 4.5 | Control pH 7.5 | Control pH 5.5 | Growth Control |
|---|---|---|---|---|---|---|---|
| Initial | 5.97 | 5.94 | 5.8 | 5.86 | 6.07 | 5.76 | 5.95 |
| 0.5 hour | 5.65 | 5.57 | 5.51 | 5.51 | 6 | 6 | 5.94 |
| 1 hour | 5.35 | 5.3 | 5.27 | 5.24 | 6.35 | 6.35 | 6.34 |
| 2 hours | 4.45 | 4.54 | 4.63 | 4.82 | 6.98 | 6.85 | 7.01 |
| 3 hours | 0 | 4.15 | 4.4 | 4.35 | 7.7 | 7.81 | 8.1 |
| 6 hours | 0 | 0 | 0 | 0 | 9.3 | 9.3 | 9.66 |
| 8 hours | 0 | 0 | 0 | 0 | 9.31 | 9.48 | 9.64 |
| 24 hours | 0 | 0 | 0 | 0 | 9.58 | 9.63 | 9.67 |
| 48 hours | 0 | 0 | 0 | 0 | 9.5 | 9.38 | 9.43 |

TABLE 11

Percentage log reduction values for *Staphylococcus aureus* time kill study

| Time | Ciprofloxacin pH 7.5 | Ciprofloxacin pH 6.5 | Ciprofloxacin pH 5.5 | Ciprofloxacin pH 4.5 |
|---|---|---|---|---|
| 0.5 hour | 5.2 | 6.2 | 4.9 | 6 |
| 1 hour | 7.7 | 10.8 | 9.1 | 10.6 |
| 2 hours | 23.2 | 23.6 | 20.2 | 17.7 |
| 3 hours | 100 | 30.1 | 24.1 | 25.8 |
| 6 hours | 100 | 100 | 100 | 100 |
| 8 hours | 100 | 100 | 100 | 100 |
| 24 hours | 100 | 100 | 100 | 100 |
| 48 hours | 100 | 100 | 100 | 100 |

Figure 5A:
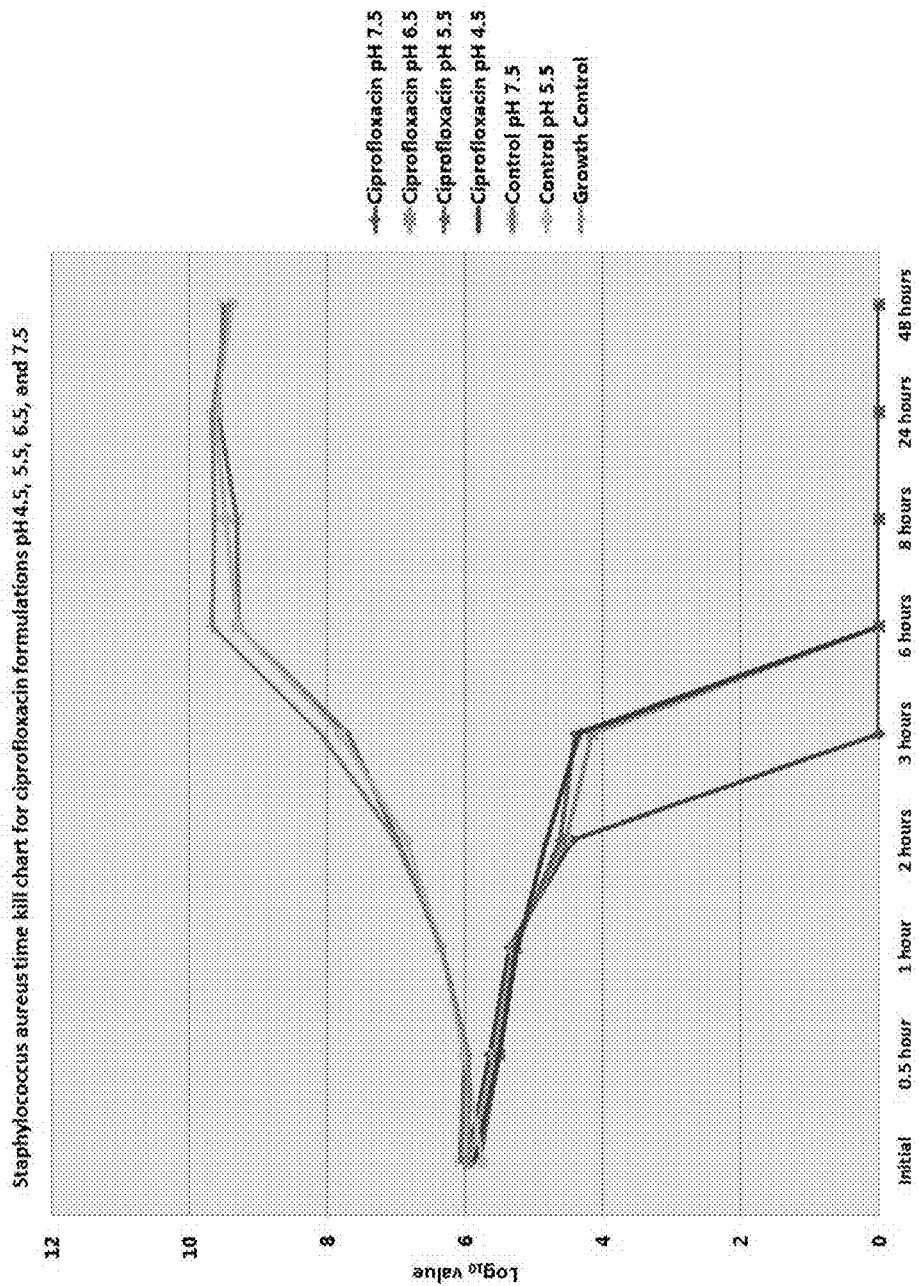
FIG. 5A is a *Staphylococcus aureus* time kill chart for ciprofloxacin formulations pH 4.5, 5.5, 6.5, and 7.5.
Figure 5B:
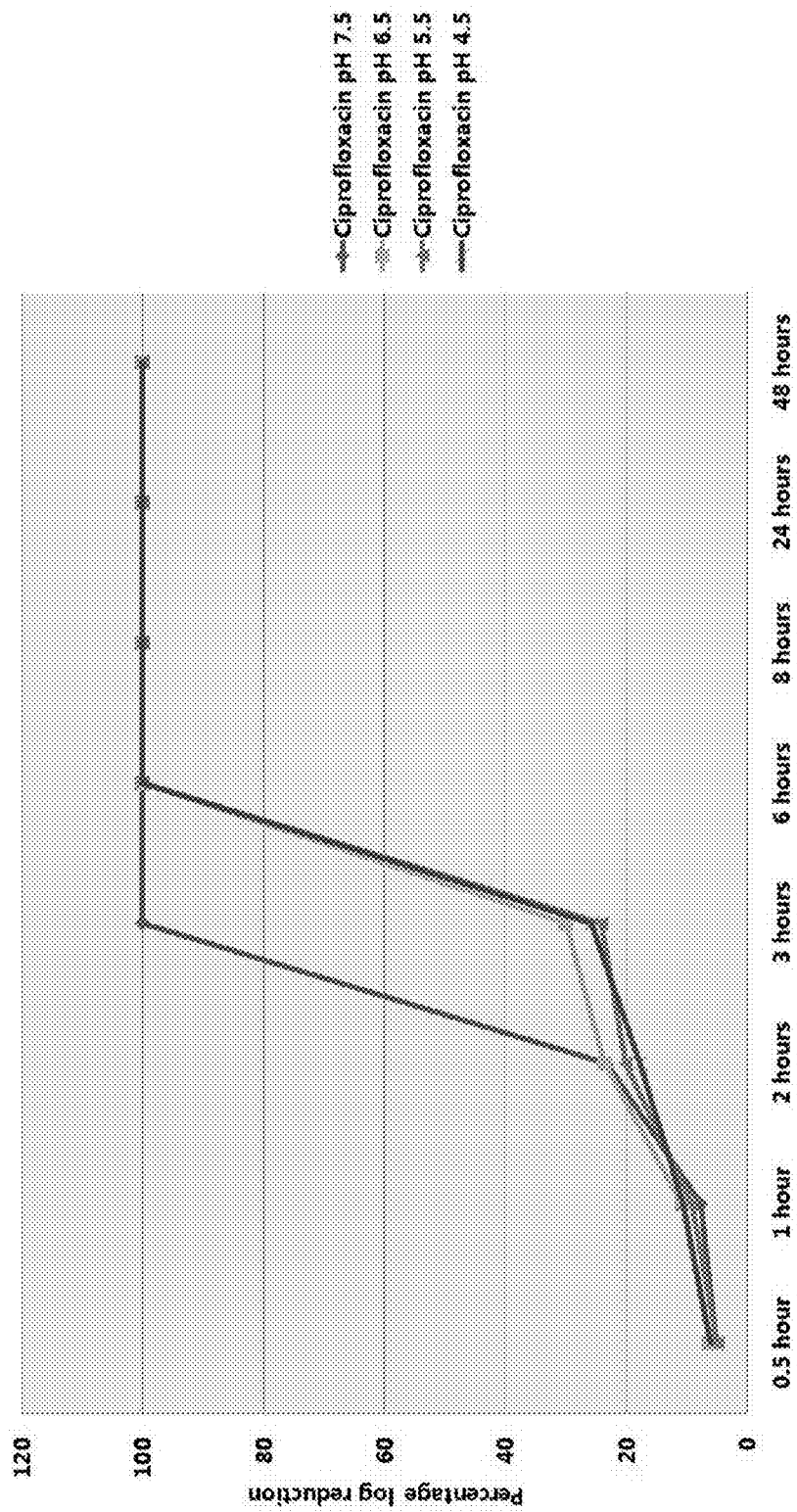
FIG. 5B is a *Staphylococcus aureus* percentage log reduction chart for ciprofloxacin formulations pH 4.5, 5.5, 6.5, and 7.5.

The *Staphylococcus aureus* time kill log$_{10}$ values and percentage reduction values are plotted as function of time in FIG. 5A and FIG. 5B, respectively.

EXAMPLE 7

*Serratia marcescens*

A time kill study for *Serratia marcescens* was conducted according to the protocol described in Example 1. The log$_{10}$ values and the percentage log reduction values for this time kill study are set forth in Tables 12 and 13, respectively.

TABLE 12

Log$_{10}$ values for *Serratia marcescens* time kill study

| Time | Ciprofloxacin pH 7.5 | Ciprofloxacin pH 6.5 | Ciprofloxacin pH 5.5 | Ciprofloxacin pH 4.5 | Control pH 7.5 | Control pH 5.5 | Growth Control |
|---|---|---|---|---|---|---|---|
| Initial | 3.98 | 4.06 | 4.22 | 4.01 | 6.04 | 6.1 | 6.11 |
| 0.5 hour | 3.29 | 3.6 | 3.51 | 3.83 | 6.14 | 6.04 | 6.11 |
| 1 hour | 2.94 | 3.09 | 3.3 | 3.65 | 6.47 | 6.24 | 6.07 |
| 2 hours | 0 | 2.7 | 3.24 | 3.35 | 6.42 | 6.7 | 6.74 |
| 3 hours | 0 | 1.35 | 3.09 | 3.09 | 7.51 | 7.44 | 7.63 |
| 6 hours | 0 | 0 | 0 | 0 | 9.04 | 9.15 | 9.3 |
| 8 hours | 0 | 0 | 0 | 0 | 9.22 | 9.35 | 9.38 |
| 24 hours | 0 | 0 | 0 | 0 | 9.12 | 9.06 | 9.1 |
| 48 hours | 0 | 0 | 0 | 0 | 7.15 | 6.84 | 6.9 |

TABLE 13

Percentage log reduction values for *Serratia marcescens* time kill study

| Time | Ciprofloxacin pH 7.5 | Ciprofloxacin pH 6.5 | Ciprofloxacin pH 5.5 | Ciprofloxacin pH 4.5 |
|---|---|---|---|---|
| 0.5 hour | 17.4 | 11.3 | 16.8 | 4.6 |
| 1 hour | 30.3 | 23.9 | 21.7 | 9 |
| 2 hours | 100 | 33.5 | 23.2 | 16.5 |
| 3 hours | 100 | 66.7 | 26.8 | 23 |
| 6 hours | 100 | 100 | 100 | 100 |
| 8 hours | 100 | 100 | 100 | 100 |
| 24 hours | 100 | 100 | 100 | 100 |
| 48 hours | 100 | 100 | 100 | 100 |

Figure 6A:
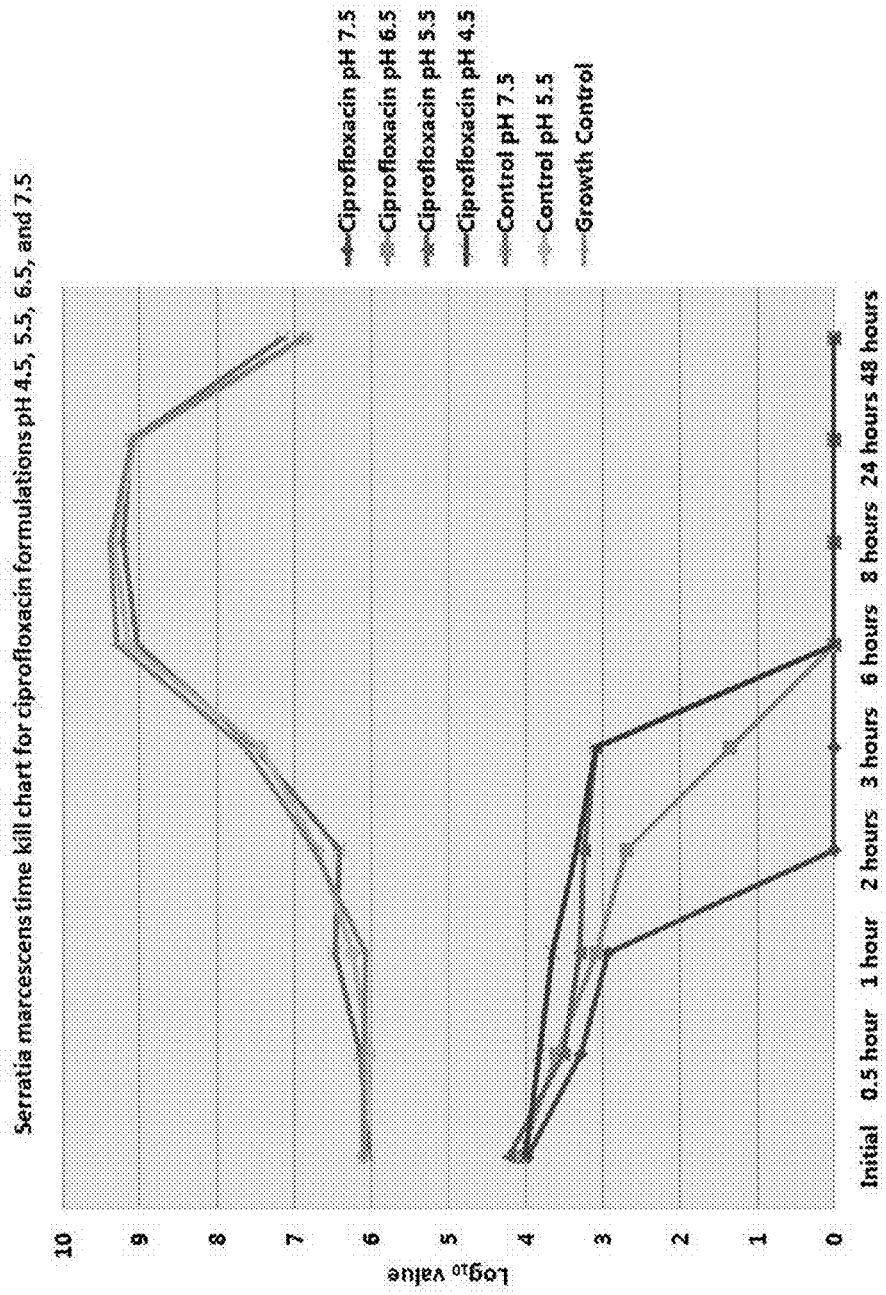
FIG. 6A is a *Serratia marcescens* time kill chart for ciprofloxacin formulations pH 4.5, 5.5, 6.5, and 7.5.
Figure 6B:
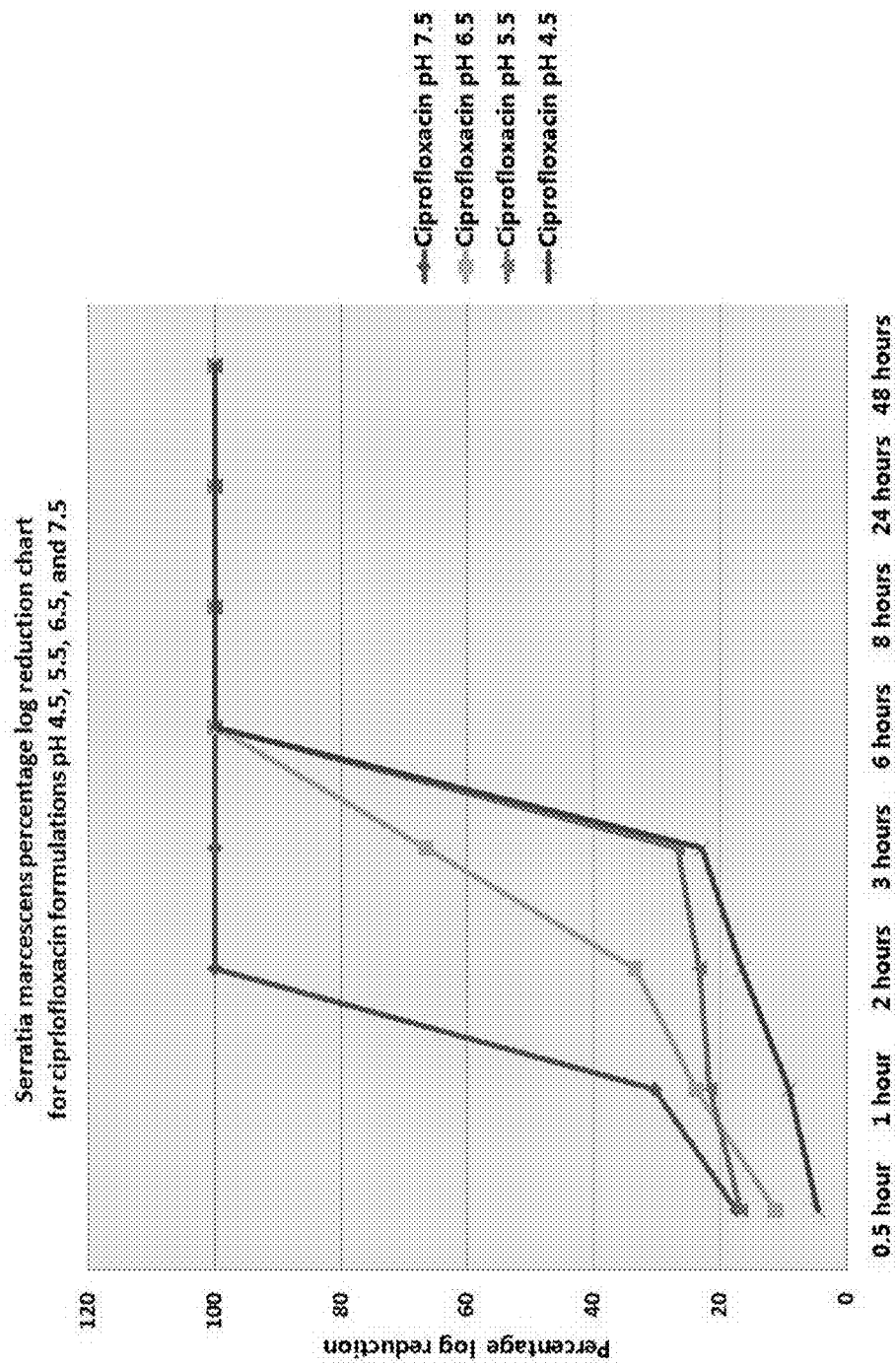
FIG. 6B is a *Serratia marcescens* percentage log reduction chart for ciprofloxacin formulations pH 4.5, 5.5, 6.5, and 7.5.

The *Serratia marcescens* time kill log$_{10}$ values and percentage reduction values are plotted as function of time in FIG. 6A and FIG. 6B, respectively.

EXAMPLE 8

*Klebisiella pneumoniae*

A time kill study for *Klebisiella pneumoniae* was conducted according to the protocol described in Example 1. The log$_{10}$ values and the percentage log reduction values for this time kill study are set forth in Tables 14 and 15, respectively.

TABLE 14

Log$_{10}$ values for *Klebisiella pneumoniae* time kill study

| Time | Ciprofloxacin pH 7.5 | Ciprofloxacin pH 6.5 | Ciprofloxacin pH 5.5 | Ciprofloxacin pH 4.5 | Control pH 7.5 | Control pH 5.5 | Growth Control |
|---|---|---|---|---|---|---|---|
| Initial | 4.44 | 4.97 | 4.72 | 4.76 | 6.11 | 6.18 | 6.2 |
| 0.5 hour | 3.63 | 3.54 | 3.39 | 4.24 | 6.13 | 5.81 | 5.87 |
| 1 hour | 3.15 | 3.35 | 3.18 | 3.65 | 5.94 | 6.04 | 5.88 |
| 2 hours | 0 | 2.7 | 2.7 | 3.39 | 6.93 | 7 | 6.39 |
| 3 hours | 0 | 1.5 | 1.35 | 2.85 | 7.54 | 7.56 | 7.75 |
| 6 hours | 0 | 0 | 0 | 1.35 | 8.57 | 9.07 | 9.14 |
| 8 hours | 0 | 0 | 0 | 0 | 9.15 | 9.2 | 9.14 |
| 24 hours | 0 | 0 | 0 | 0 | 9.15 | 9.3 | 9.3 |
| 48 hours | 0 | 0 | 0 | 0 | 9.35 | 9.3 | 9.43 |

TABLE 15

Percentage log reduction values for *Klebisiella pneumoniae* time kill study

| Time | Ciprofloxacin pH 7.5 | Ciprofloxacin pH 6.5 | Ciprofloxacin pH 5.5 | Ciprofloxacin pH 4.5 |
|---|---|---|---|---|
| 0.5 hour | 18.3 | 28.7 | 28.2 | 10.9 |
| 1 hour | 33.2 | 32.6 | 32.7 | 23.3 |
| 2 hours | 100 | 45.7 | 42.8 | 28.8 |
| 3 hours | 100 | 69.8 | 71.4 | 40.1 |
| 6 hours | 100 | 72.8 | 100 | 71.6 |
| 8 hours | 100 | 100 | 100 | 100 |
| 24 hours | 100 | 100 | 100 | 100 |
| 48 hours | 100 | 100 | 100 | 100 |

Figure 7B:
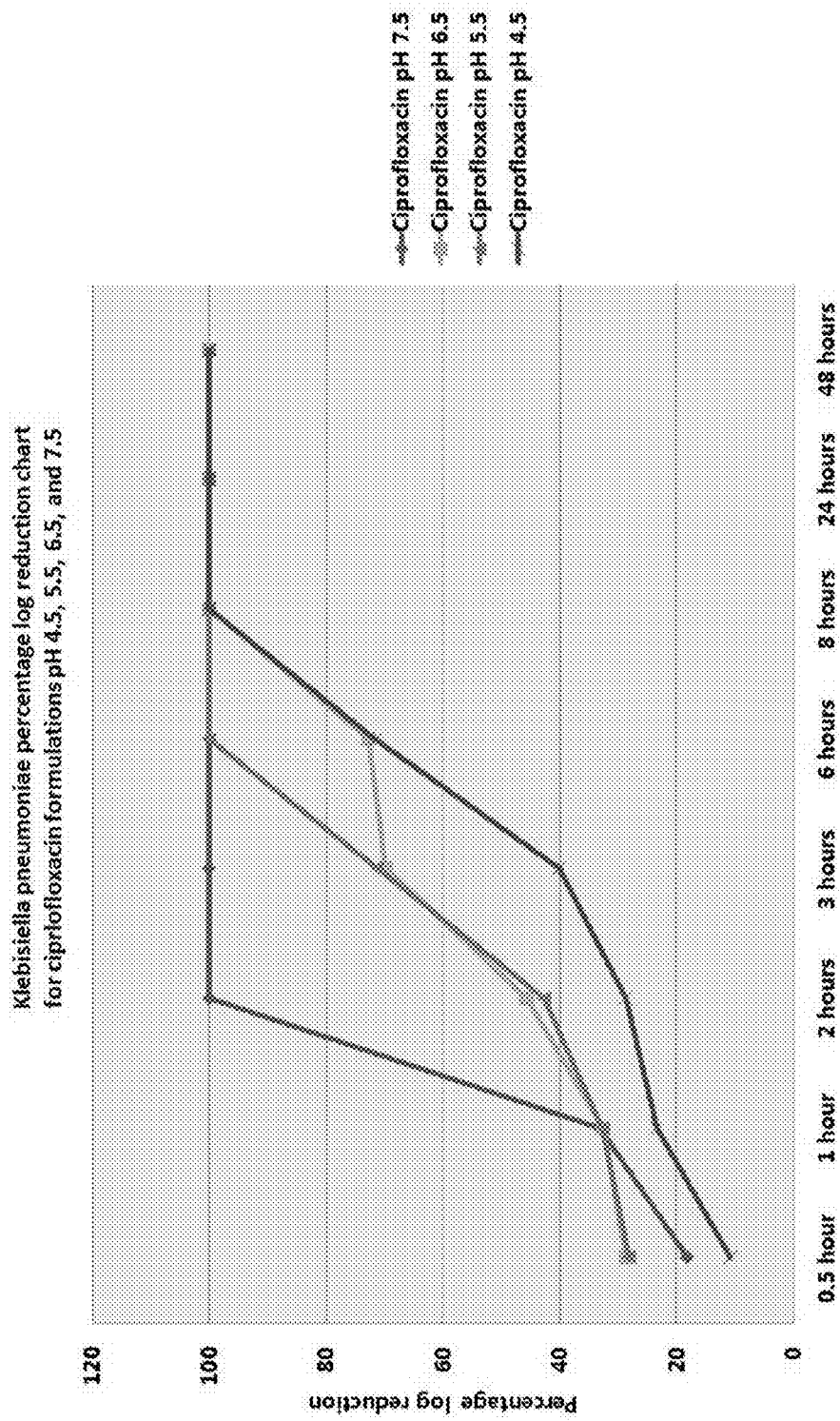
FIG. 7B is a *Klebisiella pneumoniae* percentage log reduction chart for ciprofloxacin formulations pH 4.5, 5.5, 6.5, and 7.5.

The *Klebisiella pneumoniae* time kill log$_{10}$ values and percentage reduction values are plotted as function of time in FIG. 7A and FIG. 7B, respectively.

Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A pharmaceutical composition formulated for: a. topical application to a body surface, and b. antibacterial activity localized to the body surface, the pharmaceutical composition consisting essentially of:
   a therapeutically effective amount of a non-betaine form ciprofloxacin;
   at least one member selected from the group consisting of a pH adjusting agent and a preservative;
   water; and
   a pH of from more than 6 to about 8.5,
   wherein:
   more than 10% of the non-betaine form ciprofloxacin is in the pharmaceutical composition in suspended form;
   the body surface is: at least one member of the group consisting of a dermal surface, an ophthalmic surface, a mucosal surface, and a fingernail surface, and/or in at least one member selected from the group consisting of an ear canal, an oral cavity, a pharyngeal cavity, a nasal cavity, a pulmonary cavity, a vaginal cavity, and a rectal cavity; and
   the pharmaceutical composition exhibits a more rapid onset of antibacterial activity than a comparator formulation that differs from the pharmaceutical composition by having: a pH of about 4.5 and 5% or less of the non-betaine form ciprofloxacin in suspension.

2. The pharmaceutical composition of claim 1, wherein:
   the non-betaine form ciprofloxacin is a ciprofloxacin hydrochloride and the therapeutically effective amount of the ciprofloxacin hydrochloride is from about 0.05% w/w to about 20% w/w of the composition;
   the pH adjusting agent, when present in the composition, is selected from the group consisting of a hydrochloric acid, a sulfuric acid, a phosphoric acid, a sodium hydroxide, a potassium hydroxide, a calcium hydroxide, a magnesium hydroxide, an ethanolamine, and a combination thereof; and
   the preservative, when present in the composition, is: in an amount ranging from about 0.001% w/w to about 2.5% w/w of the composition and is selected from the group consisting of a benzalkonium chloride, a lauralkonium chloride, a cetrimonium, a chlorobutanol, a methyl paraben, a propyl paraben, a phenylethyl alcohol, a borate, a sorbate, and a combination thereof.

3. The pharmaceutical composition of claim 2, further consisting essentially of at least one member selected from the group consisting of:
   an amount of an osmolality adjusting agent sufficient to provide the composition with an osmotic pressure of from about 100 mOsM to about 600 mOsM, the osmolality adjusting agent selected from the group consisting of a glycerol, a mannitol, a xylitol, a sorbitol, a dextrose, a glucose, a maltose, a trehalose, a sucrose, a cyclodextrin, a propylene glycol a, sodium chloride, a potassium chloride, a calcium chloride, a magnesium chloride, a sodium bisulfite, a sodium sulfite, a sodium sulfate, a sodium bicarbonate, a sodium carbonate, a sodium thiosulfate, a potassium acetate, a sodium acetate, a magnesium sulfate, a disodium hydrogen phosphate, a sodium dihydrogen phosphate, a potassium dihydrogen phosphate, and a combination thereof;
   from about 0.01% w/w to about 5% w/w of a viscosity building agent selected from the group consisting of a polyethylene glycol, a polyvinyl alcohol, a polyvinyl pyrrolidone, a polyvinyl alcohol, a methylcellulose, a hydroxyethylcellulose, a hydroxypropylcellulose, a guar gum, a hydroxypropyl guar gum, a gum arabic, a karaya gum, a xanthan gum, an agar, an alginic acid, a dextran, a heparin, a hyaluronic acid, a chondroitin sulfate, a starch, a chitin, a carrageenan, a polyacrylate, a casein, a gelatin, a collagen, a pectin, an elastin, and a combination thereof;
   from about 0.01% w/w to about 5% w/w of a buffer selected from the group consisting of a phosphate buffer, a citrate buffer, an acetate buffer, a carbonate buffer, a succinate buffer, a bicine buffer, a TRIS buffer, a tricine buffer, a TAPS 0 buffer, a HEPES buffer, a TES buffer, a MOPS buffer, a PIPES buffer, a cacodylate buffer, a MES buffer, and a combination thereof;
   from about 0.001% w/w to about 5% w/w of a chelating agent selected from the group consisting of a adeferoxamine, an ethylenediaminetetraacetic acid, an ethyleneglycoltetraacetic acid, and a combination thereof; and from about 0.01% w/w to about 5% w/w of a surfactant selected from the group consisting of a sorbitan, a polysorbate, a poloxamer, a sodium lauryl sulfate, a tyloxapol, and a combination thereof.

4. The pharmaceutical composition of claim 3, further consisting essentially of:

from about 0.25% w/w to about 5% w/w of the ciprofloxacin hydrochloride;

from about 0.005% w/w to about 1.0% w/w of the preservative selected from the group consisting of the benzalkonium chloride and the borate;

from about 0.001% w/w to about 1.5% w/w the sodium chloride osmolality adjusting agent;

from about 0.1% w/w to about 2.5% w/w of the hydroxyethylcellulose viscosity building agent from about 0.005% w/w to about 0.5% w/w of the ethylenediaminetetraacetic chelating agent;

from about 0.005% w/w to about 1.0% w/w of the tyloxapol surfactant, and wherein the pharmaceutical composition exhibits the more rapid onset of antibacterial activity against a bacteria selected from the group consisting of *Haemophilus influenza, Streptococcus pneumoniae, Escherichia coli, Staphylococcus aureus, Serrata marcescens*, and *Klebisiella pneumoniae*.

5. The pharmaceutical composition of claim 3, wherein the composition consists essentially of:

about 0.35% w/w of the non-betaine form ciprofloxacin hydrochloride monohydrate;

about 0.01% w/w of the benzalkonium chloride about 0.06% w/w of the boric acid;

about 0.53% w/w of the sodium chloride;

about 0.2% w/w of the hydroxyethylcellulose;

about 0.01% w/w of the sodium acetate;

about 0.1% w/w of the acetic acid;

about 0.01% w/w of the ethylenediaminetetraacetic acid; and about 0.05% w/w of the tyloxapol.

6. The pharmaceutical composition of claim 1, wherein more than 50% of the non-betaine form ciprofloxacin is in suspended form.

7. The pharmaceutical composition of claim 6, wherein more than 60% of the non-betaine form ciprofloxacin is in suspended form.

8. The pharmaceutical composition of claim 7, wherein more than 70% of the non-betaine form ciprofloxacin is in suspended form.

9. The pharmaceutical composition of claim 8, wherein more than 80% of the non-betaine form ciprofloxacin is in suspended form.

10. The pharmaceutical composition of claim 3, wherein more than 50% of the non-betaine form ciprofloxacin is in suspended form.

11. The pharmaceutical composition of claim 10, wherein more than 60% of the non-betaine form ciprofloxacin is in suspended form.

12. The pharmaceutical composition of claim 11, wherein more than 70% of the non-betaine form ciprofloxacin is in suspended form.

13. The pharmaceutical composition of claim 12, wherein more than 80% of the non-betaine form ciprofloxacin is in suspended form.

14. The pharmaceutical composition of claim 4, further consisting essentially of from 0.01% w/w to 1.5% w/w of a corticosteroid drug.

15. The pharmaceutical composition of claim 4, further consisting essentially of from 0.01% w/w to 1.5% w/w of a decongestant drug.

16. The pharmaceutical composition of claim 4, further consisting essentially of from 0.01% w/w to 1.5% w/w of a topical anesthetic.

* * * * *